United States Patent [19]
Akhavan-Tafti et al.

[11] Patent Number: 5,491,072
[45] Date of Patent: Feb. 13, 1996

[54] N-ALKYLACRIDAN CARBOXYL DERIVATIVES USEFUL FOR CHEMILUMINESCENT DETECTION

[75] Inventors: Hashem Akhavan-Tafti, Sterling Heights; Renuka Desilva, Northville; Katsuaki Sugioka, Farmington Hills, all of Mich.

[73] Assignee: Lumigen, Inc., Southfield, Mich.

[21] Appl. No.: 61,810

[22] Filed: May 17, 1993

[51] Int. Cl.$^6$ .............................. C12Q 1/28; C12Q 1/26; C12Q 1/00; C07H 5/04
[52] U.S. Cl. .................... 435/28; 435/25; 435/4; 435/19; 435/18; 435/21; 435/810; 435/968; 436/501; 436/172; 546/102; 546/108; 536/18.7
[58] Field of Search .................... 435/28, 19, 21, 435/810, 968, 25, 4, 18; 514/297; 536/18.7; 436/172, 501; 546/102, 108

[56] References Cited

U.S. PATENT DOCUMENTS 2,510,431  6/1950  Stewart et al. .............. 435/4

(List continued on next page.)

OTHER PUBLICATIONS

Worthington Enzyme Manual, C. Worthington, ED. Worthington Biochemical Corp., Freehold, N.J., 1988, pp. 155–157, 254–259.
M. S. Kaltenbach, Mikrochim. Acta, 108 205–219 (1992).
S. B. Vlasenko, A. A. Arefyev, A. D. Klimov, B. B. Kim, E. L. Gorovits, A. P. Osipov, E. M. Gavrilova, A. M. Yegorov, J., Biolumin. Chemilumin., 4, 164–176 (1989).
K. Sasamoto, Y. Ohkura, Chem. Pharm. Bull, 39(2), 411–6 (1991).
L. J. Kricka, M. DeLuca, Arch. Biochem. Biophys., 217, 674 (1983).
T. Goto, H. Fukatsu, Tetrahedron. Lett., 4299 (1969).
McCapra, F., Pure Appl. Chem., 24, 611–629 (1970).
McCapra, F., M. Roth, D. Hysert, K. A. Zaklika in Chemiluminescence and Bioluminescence, Plenum Press, New York, pp. 313–321 (1973).
McCapra, F., Prog. Org. Chem., 8, 231–277 (1971).
Steenken, S.,, Photochem. Photobiol. 11, 279–283 (1970).
Hapiot, P., et al., J. Am. Chem. Soc., 112 (4), 1337–43 (1990).
Koper, N. W., et al., Recl. Trav. Chim. Pays-Bas, 104 (11), 296–302 (1985).
Sinha, A.,, et al., J. Am. Chem. Soc., 106(23), 7291–2 (1984).
Colter, A. K., et al, Can. J. Chem., 62(9), 1780–4 (1984).
Chupakhin, O. N., et al, Dokl. Akad. Nauk SSSR, 250(4), 875–7 (1980).
Knappe, W. R., J. Pharm. Sci., 67(3), 318–20 (1978).
Digenis, G. A., et al, J. Pharm. Sci. 65(2), 247–51 (1976).
McCapra, F., Accts. Chem. Res., 9(6), 201–8 (1976).
Kinkel, T., et al, J. Biolumin. Chemilumin., 4, 136–139 (1989).
Zomer, G., et al., Anal. Chim. Acta, 227, 11–19 (1989).
Law, S.-J. et al, J. Biolumin. Chemilumin., 4, 88–98 (1989).
Whitehead, T. P., et al., Nature, 305, 158 (1983).
Thorpe, G. H., et al., Clin. Chem., 31, 1335 (1985).
Thorpe, G. H., et al., Anal. Chim. Acta, 170, 107 (1985).
Matthews, J. A., et al., Anal. Biochem., 151, 205 (1985).
Branchini, B. R., et al., in Bioluminescence and Chemiluminescence: Instrumental Applications, K. VanDyke, ed., CRC Press, Boca Raton, Fla., vol. 2, pp. 25–39, (1985).
Omote, Y., et al., Chem. Commun. 914 (1970).
Stott, R. A. W., et al., Bioluminescence and Chemiluminescence, New Perspectives, J. Scholmerich et al., EDs. pp. 237–240 (1987).
Laemmli, U. K., Nature (London), 227, 680 (1970).
Webster, 2nd Ed., p. 24, (1950).
Kaltenbach et al, Chem Abstract 118(2): 15573t (1993).
Kinkel et al, Jour Bioluminescence & Chemiluminescen, vol. 4 pp. 136–139 (1989).

*Primary Examiner*—Michael G. Wityshyn
*Assistant Examiner*—Louise N. Leary
*Attorney, Agent, or Firm*—Ian C. McLeod

[57] ABSTRACT

N-alkylacridan carboxylic acid derivative compounds (I) are used to generate chemiluminescence by the action of a peroxidase enzyme and an oxidant. The compounds I are useful in assays of all types.

68 Claims, 7 Drawing Sheets

U.S. PATENT DOCUMENTS

| | | | |
|---|---|---|---|
| 2,645,594 | 7/1953 | Tabern | 435/4 |
| 3,431,342 | 3/1969 | Haring et al. | 435/4 |
| 3,830,919 | 8/1974 | Molnar et al. | 435/4 |
| 3,917,603 | 11/1975 | Gosteli | 546/102 |
| 3,962,252 | 6/1976 | Wu et al. | 546/102 |
| 4,094,981 | 6/1978 | Wu et al. | 435/4 |
| 4,263,398 | 4/1981 | Miyashiro et al. | 435/4 |
| 4,687,747 | 8/1987 | Lin | 546/108 |
| 4,745,181 | 5/1988 | Law et al. | 536/18.7 |
| 4,918,192 | 4/1990 | Law et al. | 546/102 |
| 4,946,958 | 8/1990 | Campbell et al. | 546/102 |
| 5,110,932 | 5/1992 | Law et al. | 546/102 |
| 5,132,204 | 7/1992 | Urdea | 435/28 |
| 5,283,334 | 2/1994 | McCapra | 435/4 |
| 5,284,951 | 2/1994 | McCapra | 546/108 |
| 5,290,936 | 3/1994 | Beheshti | 546/108 |

N-ALKYLACRIDAN CARBOXYL DERIVATIVES USEFUL FOR CHEMILUMINESCENT DETECTION

BACKGROUND OF THE INVENTION

1. Field of the Invention

The present invention relates to novel N-alkylacridan carboxyl derivatives which produce light. This invention further relates to an improved method of generating light chemically (chemiluminescence) by the action of a peroxidase enzyme and an oxidant such as hydrogen peroxide with a group of N-alkylacridan carboxyl derivatives. The invention also relates to a method of greatly increasing the amount of chemiluminescence produced from this process by the use of enhancers. The invention also relates to the use of this method to detect the peroxidase enzyme. The invention also relates to the use of this method to detect hydrogen peroxide. Further, the invention relates to the use of the method to detect and quantitate various biological molecules. For example, the method may be used to detect haptens, antigens and antibodies by the technique of immunoassay, proteins by Western blotting, DNA and RNA by Southern and Northern blotting and nucleic acids by enzyme-linked nucleic acid probes. The method may also be used to detect DNA in DNA sequencing applications. The method may additionally be used to detect enzymes which generate hydrogen peroxide such as glucose oxidase, glucose-6-phosphate dehydrogenase, galactose oxidase and the like.

2. Description of Related Art

The detection and quantitation of biological molecules has been accomplished historically with excellent sensitivity by the use of radiolabeled reporter molecules. Recently numerous non-radioactive methods have been developed to avoid the hazards and inconvenience posed by these materials. Methods based on enzyme-linked analytes offer the best sensitivity since the ability to catalytically turn over substrate to produce a detectable change achieves an amplification. Substrates which generate color, fluorescence or chemiluminescence have been developed, the latter achieving the best sensitivity.

Further increases in assay sensitivity will expand the range of utility of chemiluminescence-based methods by permitting the detection of analytes present in smaller quantities or reducing the amount of time and/or reagents required to perform the assay. A way to increase the speed and sensitivity of detection in an enzymatic chemiluminescent assay is through the use of substrates which generate light with a higher efficiency or for a greater length of time.

Among the enzymes used in enzyme-linked detection methods such as immunoassays, detection of oligonucleotides and nucleic acid hybridization techniques, the most extensively used to date has been horseradish peroxidase. To take better advantage of the beneficial properties of this enzyme in analysis, new chemiluminescent substrates which permit the detection of lower amounts of enzyme would be desirable. Specifically, substrates which generate higher levels of chemiluminescence via either a higher maximum intensity or a longer duration than compounds known in the art would be advantageous.

a. Oxidation of Acridan.

Oxidation of acridan by benzoyl peroxide in aqueous solution produced chemiluminescence with very low efficiency ($\emptyset_{CL}=3\times10^{-7}$) and a mixture of products including acridine (S. Steenken, Photochem. Photobiol., 11, 279–283 (1970)). N-Methylacridan is oxidized electrochemically to N-methylacridinium ion (P. Hapiot, J. Moiroux, J. M. Saveant, J. Am. Chem. Soc., 112 (4), 1337–43 (1990); N. W. Koper, S. A. Jonker, J. W. Verhoeven, Recl. Trav. Chim. Pays-Bas, 104 (11), 296–302 (1985)). Chemical oxidation of N-alkylacridan compounds has been performed with ferricyanide ion (A. Sinha, T. C. Bruice, J. Am. Chem. Soc., 106(23), 7291–2 (1984)), certain quinones (A. K. Colter, P. Plank, J. P. Bergsma, R. Lahti, A. A. Quesnel, A. G. Parsons, Can. J. Chem., 62(9), 1780–4 (1984)), and lithium nitrite (O. N. Chupakhin, I. M. Sosonkin, A. I. Matern, G. N. Strogov, Dokl. Akad. Nauk SSSR, 250(4), 875–7 (1980)). Oxidation of an N-alkylacridan derivative has been performed photochemically with or without a flavin compound as co-oxidant (W. R. Knappe, J. Pharm. Sci., 67(3), 318–20 (1978); G. A. Digenis, S. Shakshir, M. A. Miyamoto, H. B. Kostenbauer, J. Pharm. Sci., 65(2), 247–51 (1976)).

Aryl and alkyl esters of 10-methylacridan-9-carboxylic acid undergo autoxidation to N-methylacridone in dipolar aprotic solvents under strongly basic conditions to produce chemiluminescence (F. McCapra, Accts. Chem. Res., 9(6), 201–8 (1976)). Chemiluminescence quantum yields ranged from $10^{-5}$ to 0.1 and were found to increase as the $pK_a$ of the phenol or alcohol leaving group decreased. Quantum yields in aqueous solution were significantly lower due to a competing non-luminescent decomposition of an intermediate. Addition of the cationic surfactant CTAB increased the apparent light yield 130-fold by preventing a competing dark reaction.

No reports exist on the use of peroxidase or other enzymes to oxidize acridans or substituted acridans. No reports exist on the generation of chemiluminescence from the reaction of acridans or substituted acridans with peroxidase or any other enzymes.

b. Chemiluminescent Oxidation of Acridinium Esters.

The chemiluminescent oxidation of aliphatic and aromatic esters of N-alkylacridinium carboxylic acid by $H_2O_2$ in alkaline solution is a well-known reaction. The high chemiluminescence quantum yield approaching 0.1 has led to development of derivatives with pendant reactive groups for attachment to biological molecules. Numerous chemiluminescent immunoassays and oligonucleotide probe assays utilizing acridinium ester labels have been reported.

The use of acridinium esters (AE's), especially when labeled to a protein or oligonucleotide suffers from two disadvantages. The chief problem is limited hydrolytic stability. Acridinium ester conjugates decompose steadily at or slightly above room temperature. Depending on the substitution of the leaving group storage at −20° C. may be required for extended storage.

A second disadvantage of acridinium esters is the tendency to add nucleophiles such as water at the 9-position to spontaneously form a pseudo-base intermediate which is non-luminescent and decomposes in a pH-dependent manner in a dark process. In practice the pH of solutions containing acridinium esters must be first lowered to reverse pseudo-base formation and then raised in the presence of $H_2O_2$ to produce light.

Recently amides, thioesters and sulfonamides of N-alkylacridinium carboxylic acid have also been prepared and shown to emit light when oxidized under these conditions (T. Kinkel, H. Lubbers, E. Schmidt, P. Molz, H. J. Skripczyk, J. Biolumin. Chemilumin., 4, 136–139 (1989); G. Zomer, J. F. C. Stavenuiter, Anal. Chim. Acta, 227, 11–19 (1989)). These modifications of the leaving group only partially improve the storage stability performance.

A more fundamental limitation to the use of acridinium esters as chemiluminescent labels lies in the fact that when used as direct labels, only up to at most about 10 molecules can be attached to protein or oligonucleotide. Coupled with the quantum efficiency for producing a photon ($\leq 10\%$), an acridinium ester-labeled analyte can generate at most one photon of light. No further improvement in signal generating ability is possible.

An attempt to increase the number of acridinium ester molecules associated with an analyte in an immunoassay was made by constructing an antibody-liposome conjugate wherein the liposome contained an unspecified number of AE's (S. -J. Law, T. Miller, U. Piran, C. Klukas, S. Chang, J. Unger, *J. Biolumin. Chemilumin.*, 4, 88–98 (1989)). Only a modest increase in signal was observed over a comparable assay using directly labeled AE's.

There is no known use of a peroxidase or other enzyme in conjunction with acridinium ester chemiluminescence.

c. Chemiluminescent Detection of Horseradish Peroxidase.

Amino-substituted cyclic acylhydrazides such as luminol and isoluminol react with $H_2O_2$ and a peroxidase enzyme catalyst (such as horseradish peroxidase, HRP) under basic conditions with emission of light. This reaction has been used as the basis for analytical methods for the detection of $H_2O_2$ and for the peroxidase enzyme. Various enhancers have also been employed in conjunction with the use of luminol to increase the intensity of light emitted. These include D-luciferin (T. P. Whitehead, G. H. Thorpe, T. J. Carter, C. Groucutt, L. J. Kricka, *Nature*, 305, 158 (1983)) and p-iodophenol and p-phenylphenol (G. H. Thorpe, L. J. Kricka, S. B. Mosely, T. P. Whitehead, *Clin. Chem.*, 31, 1335 (1985)). To date, the only other chemiluminescent compound oxidized by a peroxidase enzyme and a peroxide is a hydroxy-substituted phthalhydrazide (Akhavan-Tafti co-pending U. S. patent application Ser. No. 965,231, filed Oct. 23, 1992).

The mechanism of oxidation of phthalhydrazides by the combination of a peroxide and a peroxidase enzyme is very complex and remains the subject of intense debate. This difficulty has hampered the development of new chemiluminescent reactions catalyzed by peroxidases. Nevertheless, the enzyme horseradish peroxidase has found use in enzyme immunoassays and DNA hybridization assays with chemiluminescent detection using luminol or isoluminol as substrate (T. P. Whitehead, G. H. Thorpe, T. J. Carter, C. Groucutt, L. J. Kricka, *Nature*, 305, 158 (1983); G. H. Thorpe, L. J. Kricka, S. B. Mosely, T. P. Whitehead, *Clin. Chem.*, 1335 (1985); G. H. Thorpe, S. B. Mosely, L. J. Kricka, R. A. Stott, T. P. Whitehead, *Anal. Chim. Acta*, 170, 107 (1985), and J. A. Matthews, A. Batki, C. Hynds, L. J. Kricka, *Anal. Biochem.*, 151, 205, (1985)). Commercially available kits for conjugation of HRP with enhanced luminol chemiluminescent detection are available.

Synthetic peptide-isoluminol derivatives such as t-Boc-alanylalanylphenylalanylisoluminolamide are substrates for the protease enzymes chymotrypsin, trypsin and thrombin. Reaction of compounds of this type with a protease enzyme liberates isoluminol which then can react with a peroxidase enzyme and $H_2O_2$ to generate chemiluminescence. (B. R. Branchini, G. M. Salituro, in Bioluminescence and Chemiluminescence: Instrumental Applications, K. Van Dyke, ed., CRC Press, Boca Raton, Fla., Volume 2, pp. 25–39, (1985)).

Urdea U.S. Pat. No. 5,132,204 describes a stable 1,2-dioxetane which rapidly decomposes with emission of chemiluminescence after the consecutive removal of protecting groups by HRP and alkaline phosphatase from a phenol moiety. The doubly protected compound is, however, also chemiluminescent in the absence of enzyme through slow thermal decomposition or hydrolysis of the protecting group. No examples involving N-alkylacridan carboxyl derivatives were shown.

OBJECTS

It is therefore an object of the present invention to provide a method and N-alkylacridan carboxyl derivatives for use in generating chemiluminescence by the action of a peroxidase enzyme for the detection of biological materials and compounds. It is also an object of the present invention to provide a method and kit using N-alkylacridan carboxyl derivatives in solution or on surfaces such as membranes for use in generating chemiluminescence by the action of a peroxidase enzyme for the detection of peroxidase enzymes and enzyme-conjugates. Additionally, it is an object of the present invention to provide a method and kit using N-alkylacridan carboxyl derivatives for use in generating chemiluminescence by the action of a peroxidase enzyme for use in nucleic acid assays in solution and on surfaces. Further, it is an object of the present invention to provide a method and kit using N-alkylacridancarboxylic acid derivatives for use in generating chemiluminescence by the action of a peroxidase enzyme for detection of proteins in Western blots and DNA in Southern blots and other DNA hybridization assays.

Figure 7A:
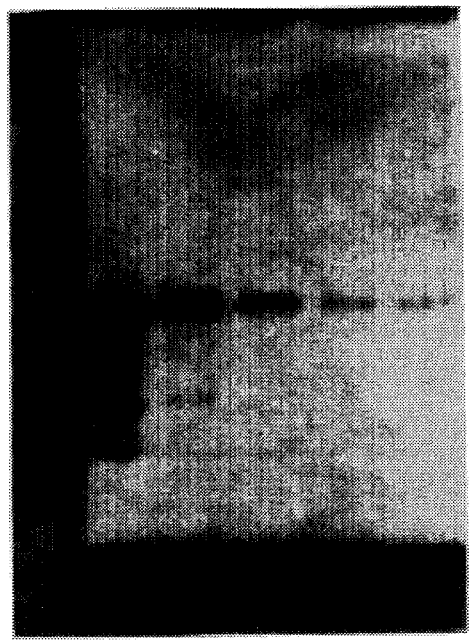
Figure 7B:
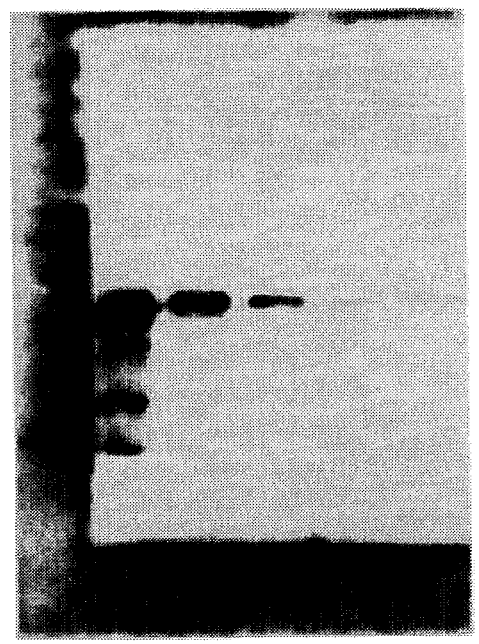

FIGS. 7A and 7B show the result of a Western blot analysis of human transferrin on nitrocellulose with chemiluminescent detection using fractionated goat anti-human transferrin serum, rabbit anti-goat IgG-peroxidase conjugate, NaBO₃ and 1b. Human transferrin loaded into each slot was ,(1) 5000 pg, (2) 1000 pg, (3) 200 pg, (4) 50 pg and (5) 20 HAT pg. The blots were exposed to X-OMAT AR (Kodak, Rochester, N.Y.) x-ray film (7A) for 7 se. HAT after a 20 HAT min incubation or to OMC x-ray film (7B) for 30 sec. HAT after a 40 HAT min incubation.

DESCRIPTION OF THE PREFERRED EMBODIMENTS

The present invention relates to an acridan of the formula

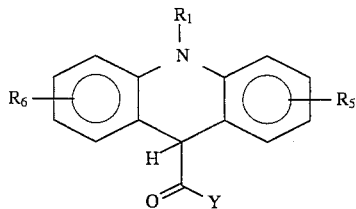

wherein R₁ is selected from alkyl, heteroalkyl and aralkyl groups, wherein R₅ and R₆ are selected from the group consisting of hydrogen and non-interfering substituents and wherein Y is a leaving group which allows the production of light from the acridan by reaction with a peroxide and a peroxidase.

The present invention relates to a method for producing chemiluminescence which comprises reacting a peroxide compound and a peroxidase with an acridan of the formula

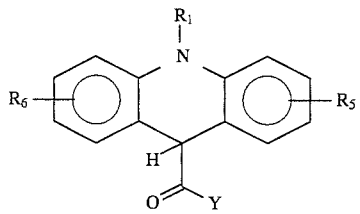

wherein R₁ is selected from alkyl, heteroalkyl and aralkyl groups, wherein R₅ and R₆ are selected from the group consisting of hydrogen and non-interfering substituents, wherein Y is a leaving group which allows the production of light from the acridan by reaction with a peroxide and a peroxidase.

The present invention also relates to a reagent composition which generates light in the presence of a peroxidase which comprises:

(a) an acridan of the formula:

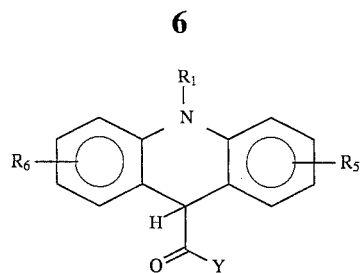

wherein R₁ is selected from alkyl, heteroalkyl and aralkyl groups, wherein R₅ and R₆ are selected from the group consisting of hydrogen and non-interfering substituents and wherein Y is a leaving group which allows the production of light from the acridan by reaction with a peroxide and a peroxidase;

(b) optionally a phenolic compound which enhances light production from the acridan;

(c) a peroxide compound which participates in the reaction of the acridan with the peroxidase;

(d) a chelating agent which prevents the peroxide compound from reacting prior to addition of the peroxidase to the composition; and (e) a nonionic surfactant.

The present invention also relates to in an improved method for detecting an analyte in an assay procedure by a chemiluminescent reaction, the improvement which comprises reacting acridan with a peroxide and a peroxidase to produce light for detecting the analyte wherein the acridan is of the following formula

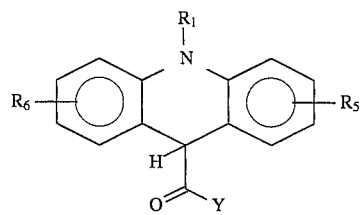

wherein R₁ is selected from alkyl, heteroalkyl and aralkyl groups, wherein R₅ and R₆ are selected from the group consisting of hydrogen and non-interfering substituents and wherein Y is a leaving group which allows the production of light from the acridan by reaction with a peroxide and a peroxidase.

The present invention also relates to an improved method for detecting an analyte in an assay procedure by a chemiluminescent reaction, the improvement which comprises:

(a) providing a reagent composition which generates light in the presence of a peroxidase which comprises: an acridan of the formula:

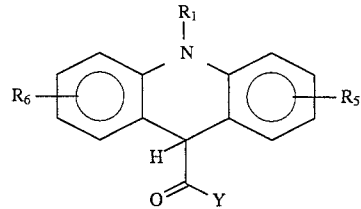

wherein R₁ is selected from alkyl, heteroalkyl and aralkyl groups, wherein R₅ and R₆ are selected from the group consisting of hydrogen and non-interfering substituents and wherein Y is a leaving group which allows the production of light from the acridan by reaction with a peroxide and a peroxidase; optionally a phenolic compound which enhances light production from the acridan; a peroxide compound which participates in the reaction of the acridan with the peroxidase; a chelating agent which prevents the peroxide compound from reacting prior to the addition of the peroxidase to the composition; and a nonionic surfactant; and (b) adding a peroxidase to the reagent composition so that light is produced for detecting the analyte.

The present invention also relates to a kit for detecting an analyte in an assay procedure by a chemiluminescent reaction to produce light which comprises in separate containers:

(a) an acridan of the formula:

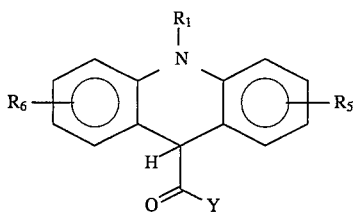

wherein $R_1$ is selected from alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase; and (b) a peroxidase enzyme, wherein the light is detected in the assay procedure by reacting the reagent composition with the peroxidase.

The present invention also relates to a kit for detecting an analyte in an assay procedure by a chemiluminescent reaction to produce light which comprises in separate containers:

(a) a reagent composition the components of which may be in a single or multiple containers which generates light in the presence of a peroxidase which comprises: an acridan of the formula:

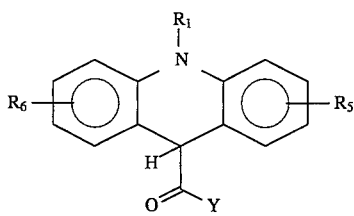

wherein $R_1$ is selected from alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase; optionally a phenolic compound which enhances light production from the acridan; a peroxide compound which participates in the reaction of the acridan with the peroxidase; a chelating agent which prevents the peroxide compound from reacting prior to the addition of the peroxidase to the composition; and a nonionic surfactant; and (b) a peroxidase enzyme, wherein the light is detected in the assay procedure by reacting the reagent composition with the peroxidase.

The present invention also relates to an improved method for detecting hydrogen peroxide in an assay procedure by a chemiluminescent reaction, the improvement which comprises reacting hydrogen peroxide and a peroxidase with an acridan of the formula:

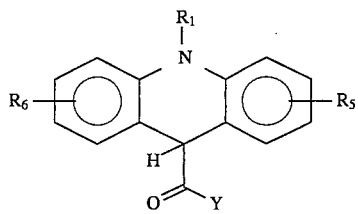

wherein $R_1$ is selected from alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase.

The preferred compounds of the present invention are compounds 1a to 1e as follows:

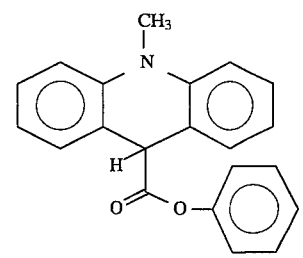
1a

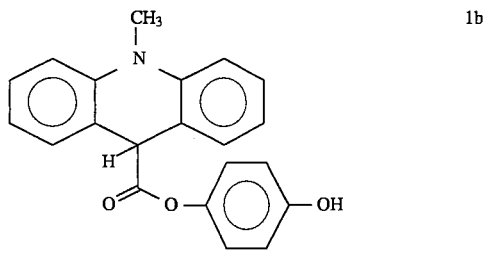
1b

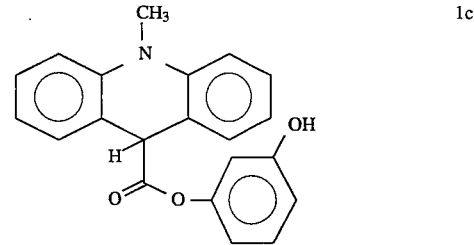
1c

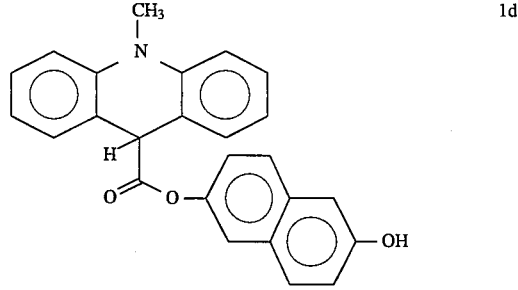
1d

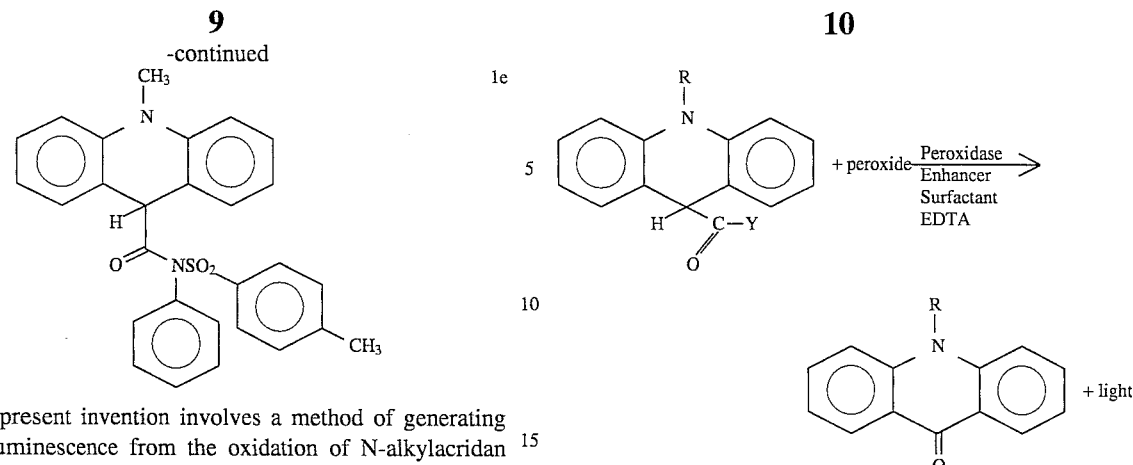

The present invention involves a method of generating chemiluminescence from the oxidation of N-alkylacridan carboxyl acid derivatives (I) by the action of a peroxidase enzyme, a peroxide compound and enhancers. The invention also relates to the use of this method to detect the peroxidase enzyme with high sensitivity. Further, the invention relates to the use of the method to detect and quantitate various biological molecules which are bound to this enzyme by chemical bonds or through physical interactions. The intensity of the resulting chemiluminescence provides a direct measure of the quantity of labeled organic or biological molecule. For example, the method may be used to detect haptens, antigens and antibodies by the technique of immunoassay, proteins by Western blotting, DNA and RNA by Southern and Northern blotting and nucleic acids by enzyme-linked nucleic acid probes. The method may also be used to detect DNA in DNA sequencing applications. The method may be used to detect hydrogen peroxide generated by enzymes such as glucose oxidase, glucose-6-phosphate dehydrogenase, galactose oxidase, galactose-6-phosphate dehydrogenase, and amino acid oxidase. The method may also therefore be used as a means to detect the enzymes mentioned above which generate hydrogen peroxide.

The reaction of the present invention may be carried out in solution such as an aqueous buffer or on the surface of a solid support such as a bead, tube, microwell plate or a membrane as is well known to those skilled in the art. When the detection is to be performed on a membrane, said membrane may optionally be provided in the kit.

The detection of chemiluminescence from the oxidation of an N-alkylacridan carboxyl acid derivative by hydrogen peroxide catalyzed by a peroxidase enzyme can be accomplished with good sensitivity. Enhancement of this reaction by incorporation of chemiluminescence-enhancing substances has permitted the measurement of chemiluminescence using still lower levels of the peroxidase enzyme. Coupling this enzyme to a biological molecule of interest then permits the detection of this biological molecule with great sensitivity.

The preferred amounts of the various ingredients in the composition of the present invention are set forth in Table I.

TABLE I

| | |
|---|---|
| Acridan I | 0.01–10 mM |
| Phenol Enhancer | 0.001–10 mM |
| Surfactant | 0.01–5% |
| Peroxide | 0.01–10 mM |
| EDTA | 0.01–5 mM |

The generalized reaction used to produce light using the N-alkylacridan carboxyl acid derivatives (I) is as follows:

An unexpected finding of the present invention is that N-alkylacridan carboxyl acid derivatives (I) are oxidized by peroxidase enzymes in the presence of a peroxide to produce chemiluminescence. The chemiluminescence is believed to arise from the excited state of the N-alkylacridone. N-alkylacridan carboxyl derivatives which were found to undergo the reaction include esters, especially aromatic esters, and sulfonamides. Other derivatives which provide a leaving group whose conjugate acid has a pKa below about 16 such as thioesters and alkyl esters are contemplated. N-alkylacridan carboxyl derivatives bearing substituents on the aromatic groups of the acridan compound can produce light in the same manner. Non-interfering substituents such as alkyl, alkoxyl, aralkyl, heteroalkyl and carbon and/or heteroatom containing groups which provide a reactive group for attachment to other molecules or which provide improved water solubility can be included in one or both of the aromatic rings.

Further it has been discovered that incorporation of certain substituted phenol compounds in combination with nonionic surfactants into the reaction mixture enhances the chemiluminescence produced in the presence of added peroxidase and peroxide. Phenolic compounds found to enhance the amount of chemiluminescence produced in the reaction of N-alkylacridan carboxyl derivatives (I) with a peroxide compound and a peroxidase enzyme include but are not limited to: p-phenylphenol, p-iodophenol, p-bromophenol, p-hydroxycinnamic acid, 2-naphthol and 6-bromo-2-naphthol. Significantly, the phenol enhancers are effective in promoting the reaction of the hydroxyaryl acridan esters, which themselves contain a phenol substituent.

A key consideration in developing ultrasensitive detection systems is to provide the largest signal possible through amplification as, for example, by use of an enzyme as the detectable substance while maintaining the lowest possible level of background signal in relation to the signal to be measured. Accordingly, additives which suppress the generation of chemiluminescence from the reaction of hydrogen peroxide and N-alkylacridan carboxyl derivatives (I) in the absence of peroxidase enzymes are employed to improve the utility of the invention. It has also been found that surfactants such as nonionic surfactants improve the utility of the present invention by providing a better signal to background ratio. The improvement occurs through minimizing the background chemiluminescence in the absence of added peroxidase, possibly due to a slowing of the autoxidative decomposition of the acridan derivative.

An additional aspect of the invention is the use of hydroxy-substituted aryl ester leaving groups The additional hydroxy substituent provides increased stability to the ester function compared to other functional groups especially at pH values where the phenol is substantially ionized. Moreover, under the action of the peroxidase enzyme and peroxide, the hydroxyaryl acridan esters undergo a rapid and efficient chemiluminescent reaction.

The preferred system involves a solution in an aqueous buffer containing 1) a phenol enhancer 2) a peroxide compound wherein the peroxide compound may be hydrogen peroxide, urea peroxide, or a perborate salt, 3) 4'-hydroxyphenyl-10-methylacridan-9-carboxylate, 4) a cation complexing agent wherein the agent may be selected from the group consisting of chelating agents such as ethylenediaminetetraacetic acid (EDTA), diethylenetriaminepentaacetic acid (DTPA), or ethylenebis(oxyethylenenitrilo)-tetraacetic acid (EGTA) and their salts, and 5) a surfactant such as the anionic surfactant sodium dodecyl sulfate (SDS), or preferably a nonionic surfactant such as polyoxyethylenated alkylphenols, polyoxyethylenated alcohols, polyoxyethylenated ethers, polyoxyethylenated sorbitol esters and the like.

In a preferred method of practicing the present invention, an aqueous buffer solution with a pH in the range of 8–10 containing 4'-hydroxyphenyl-10 -methylacridan-9-carboxylate at a final concentration from about 0.01M to $1\times10^{-4}$M, a phenol compound such as p-phenylphenol at a final concentration from about 0.01M to $1\times10^{-6}$M and a nonionic surfactant at a final concentration from about 5% to 0.01% (v/v) is mixed with a second solution in water or aqueous buffer containing a peroxide source such as hydrogen peroxide or, preferably, a perborate salt and a cation complexing agent such as EDTA at a final concentration from about $1\times10^{-3}$M to $1\times10^{-5}$M to form the detection reagent solution. This solution is contacted with the peroxidase enzyme which may either be in solution or adhered to a solid support. Optimum concentrations of reagents can easily be determined individually for each composition. The concentration of enhancer in particular is optimized for each different enhancer used in order to produce the maximum enhancement of light emission.

Significant advantages of N-alkyl-acridancarboxylic acid derivatives (I) and compositions of the present invention containing them is the increased sensitivity of detection of the peroxidase enzyme. Comparative experiments show a ten-fold lowering of the detection limit of HRP using a reagent composition of this invention compared to the enhanced luminol system. A second advantage is the wide dynamic range of measurement of peroxidase concentration possible. An additional advantage of N-alkylacridancarboxylic acid derivatives (I) is their thermal and photochemical stability and ease of purification. The most widely known chemiluminescent substrates or peroxidase enzymes known in the prior art, aminoaryl cyclic diacylhydrazides such as luminol and compositions containing them are readily decomposed by room light leading to loss of sensitivity and poor reproducibility when used in chemiluminescence detection schemes (Y. Omote, H. Yamamoto, N. Sugiyama, *Chem. Commun.*, 914 (1970)). Aminoaryl cyclic diacylhydrazides are difficult to prepare and maintain in a state of high purity and must either be protected from light or purified immediately before use (R. A. W. Stott, L. J. Kricka, *Bioluminescence and Chemiluminescence, New Perspectives*, J. Scholmerich, et al, Eds., pp. 237–240 (1987)). Still another advantage of the use of certain N-alkylacridan carboxyl derivatives (I) compared to prior compounds is the extended duration of chemiluminescence. Extending the duration simplifies the measurement by obviating the need for precise reaction timing and increases the sensitivity of detection when using film-based detection methods.

EXAMPLES

1. Synthesis of Acridan Derivative 1a

Phenyl acridine-9-carboxylate.

Acridine-9-carboxylic acid (1 g, 4.1 mmol) was suspended in thionyl chloride (5 mL) and the reaction mixture was refluxed for 3 hours. The solvent was removed under reduced pressure leaving a yellow solid which was dissolved in methylene chloride and pyridine (350 μL) under argon. This solution was cooled in an ice bath and a solution of phenol (0.78 g, 8.2 mmol) in methylene chloride was added dropwise. The reaction mixture was stirred overnight at room temperature. After evaporation of solvent, the residue was redissolved in ethyl acetate and washed with water. The organic layer was dried over $MgSO_4$ and concentrated to obtain a crude material which was chromatographed on silica gel (30% ethyl acetate/hexane) to yield the pure product as a yellow solid. $^1$H NMR (CDCl$_3$) δ7.35–7.57 (m, 5H), 7.63–8.37 (m, 8H).

Phenyl 10-methylacridinium-9-carboxylate trifluoromethanesulfonate.

Phenyl acridine-9-carboxylate (530 mg, 1.7 mmol) was dissolved in methylene chloride (5 mL) under argon and methyl trifluoromethanesulfonate (1 mL, 8.8 mmol) was added. The solution was stirred overnight at room temperature to yield a thick yellow precipitate. This precipitate was filtered, washed with ether and dried to obtain the product as yellow crystals. $^1$H NMR (acetone-d$_6$) δ5.22 (s, 3H), 7.47–7.71 (m, 5H), 8.23–9.07 (m, 8H).

Phenyl 10-methylacridan-9-carboxylate (1a).

Phenyl 10-methylacridinium-9-carboxylate trifluoromethanesulfonate (10 mg, 0.022 mmol) was suspended in absolute ethanol (10 mL) and the mixture was refluxed for 15 min to obtain a clear solution. Ammonium chloride (88 mg, 1.6 mmol) was added by portions to the solution followed by zinc (108 mg, 1.6 mmol). Addition of zinc caused the yellow color of the solution to disappear immediately. The colorless solution was refluxed for 2 h. TLC of the reaction mixture showed complete conversion to a non-polar material. The solution was filtered and precipitate was washed with ethanol (3×20 mL). The filtrate was concentrated to obtain an off-white solid which was redissolved in methylene chloride and washed with water (2×15 mL). The organic layer was dried over $Na_2SO_4$ and concentrated to yield the crude product which was purified by preparative TLC using (30% ethyl acetate:hexane). Pure product was obtained as an off-white solid. $^1$H NMR (CDCl$_3$) δ3.38 (s, 3H), 5.16 (s, 1H), 6.89–7.37 (m, 13H); $^{13}$C NMR (CDCl$_3$) δ33.29, 49.72, 112.93, 120.19, 121.36, 125.73, 128.67, 129.16, 129.26, 142.37, 151.04, 170.22.

2. Synthesis of Acridan Derivative 1b 4-(Tert-Butyldimethylsilyloxy)phenol.

To a solution of hydroquinone (1.0 g, 0.9 mmol) and tert-butyldimethylsilyl chloride (1.4 g, 0.9 mmol) in 5 mL of dry DMF was gradually added imidazole (1.2 g, 1.8 mmol) and the solution was stirred for 1 hour. TLC analysis (silica gel, 20% ethyl acetate/hexane) showed completion of reaction. The solution was poured into 25 mL of water and extracted with 3×25 mL of ether. The combined ether solutions were dried over anhydrous $MgSO_4$. Evaporation of solvent gave an oil which was chromatographed on silica using 20% ethyl acetate/hexane to give the product as a white solid in 70% yield: $^1$H NMR (CDCl$_3$) δ0.145 (s, 6H), 0.956 (s, 9H), 4.47 (bs, 1H), 6.68 (s, 4H); $^{13}$C NMR (CDCl$_3$) δ–4.48, 18.21, 25.74, 115.93, 120.55, 120.81, 149.78.

4'-(tert-Butyldimethylsilyloxy)phenyl acridine-9-carboxylate.

Acridine-9-carboxylic acid (800 mg, 3.8 mmol) was suspended in thionyl chloride (5 mL) and reaction mixture was refluxed for 3 hours. The solvent was removed under reduced pressure to obtain a yellow solid which was dissolved in methylene chloride and pyridine (1.5 mL) under argon. This solution was cooled in an ice bath and a solution of 4-(tert-butyldimethylsilyloxy)phenyl (1.2 g, 5.3 mmol) in methylene chloride was added dropwise. The reaction mixture was stirred overnight at room temperature. The solution was diluted with more methylene chloride and washed with water. The organic layer was dried over MgSO$_4$ and concentrated to obtain a crude material which was chromatographed on silica gel (25% ethyl acetate/hexane) to yield the pure product as a yellow solid. $^1$H NMR (CDCl$_3$) δ0.257 (s, 6H), 1.026 (s, 9H), 6.96–7.34 (dd, 4H), 7.64–8.34 (m, 8H); $^{13}$C NMR (CDCl$_3$) δ–4.38, 18.27, 25.72, 120.96, 122.19, 122.45, 127.52, 127.96, 130.57, 144.47, 148.56, 154.03, 166.15, 204.64.

4'-Hydroxyphenyl 10-methylacridinium-9-carboxylate trifluoromethanesulfonate.

4-(tert-Butyldimethylsilyloxy)phenylacridine-9-carboxylate (410 mg, 0.98 mmol) was dissolved in methylene chloride (5 mL) under argon and methyl trifluoromethanesulfonate (558 μL, 4.9 mmol) was added. The yellow solution turned into dark brown. After stirring the solution for 2 hours at room temperature a precipitate appeared and color of solution changed back to yellow. Solution was stirred overnight at room temperature to yield a thick yellow precipitate. This precipitate was filtered, washed with ether and dried to obtain the product as yellow crystals. $^1$H NMR (acetone-d$_6$) δ5.24 (s, 3H), 7.02–7.53 (dd, 4H), 8.26–9.07 (m, 8H).

4'-Hydroxyphenyl 10-methylacridan-9-carboxylate (1b).

4'-Hydroxyphenyl-10-methyl acridinium-9-carboxylate trifluoromethanesulfonate (500 mg, 1 mmol) was suspended in absolute ethanol (70 mL) and solution was refluxed for 30 min. Ammonium chloride (5.6 g, 0.104 mol) was added by portions to the heterogeneous solution followed by zinc (6.8 g, 0.104 mol). The yellow color of the solution disappeared immediately after the addition of zinc. The colorless solution was refluxed for 3 hr. TLC of the reaction mixture showed complete conversion to a nonpolar material. The solution was filtered and the precipitate was washed with ethanol (3×30 mL). The solution was concentrated to obtain an off-white solid which was redissolved in methylene chloride and washed with water (2×30 mL). The organic layer was dried over Na$_2$SO$_4$ and concentrated to yield the product as an off-white solid. $^1$H NMR (CDCl$_3$) δ3.42 (s, 3H), 4.69 (s, 1H), 5.16 (s, 1H), 6.65–6.78 (dd, 4H), 6.97–7.37 (m, 8H).

3. Synthesis of Acridan Derivative 1c 3-(tert-butyldimethylsilyloxy)phenol.

To a solution of resorcinol (1.0 g, 0.9 mmol) and tert-butyldimethylsilyl chloride (1.4 g, 0.9 mmol) in 5 mL of dry DMF was gradually added imidazole (1.2 g, 1.8 mmol) and the solution was stirred for 1 hour. TLC analysis (silica gel, 20% ethyl acetate/hexane) showed completion of reaction. The solution was poured into 25 mL of water and extracted with 3×25 mL of ether. The combined ether solutions were dried over anhydrous MgSO$_4$. Evaporation of solvent gave an oil which was chromatographed on silica using 20% ethyl acetate/hexane to give the product as a white solid in 70% yield: $^1$H NMR (CDCl$_3$) δ0.199 (s, 6H), 0.983 (s, 9H), 6.39–7.09 (m, 4H).

3'-(tert-Butyldimethylsilyloxy)phenyl acridine-9-carboxylate.

Acridine-9-carboxylic acid (700 mg, 3.3 mmol) was suspended in thionyl chloride (5 mL) and reaction mixture was refluxed for 3 hours. The solvent was removed under reduced pressure to obtain a yellow solid which was dissolved in methylene chloride and pyridine (355 μL) under argon. This solution was cooled in an ice bath and a solution of 4-(tert-butyldimethylsilyloxy)phenol (400 mg, 5.3 mol) in methylene chloride was added dropwise. Reaction mixture was stirred overnight at room temperature. After evaporation of solvent, the residue was redissolved in ethyl acetate and washed with water. The organic layer was dried over MgSO$_4$ and concentrated to obtain a crude material which was chromatographed on silica gel (30% ethyl acetate/hexane) to yield the pure product as an off-white solid. $^1$H NMR (CDCl$_3$) δ0.273 (s, 6H), 1.026 (s, 9H), 6.84–8.36 (m, 12H).

3'-Hydroxyphenyl 10-methylacridinium-9-carboxylate trifluoromethanesulfonate.

3'-(tert-Butyldimethylsilyloxy)phenylacridine-9-carboxylate (110 mg, 0.025 mmol) was dissolved in methylene chloride (5 mL) under argon and methyl trifluoromethanesulfonate (145 μL, 1.2 mmol) was added. The solution was stirred overnight at room temperature to yield a thick yellow precipitate. This precipitate was filtered, washed with chloroform and dried to obtain the product as yellow crystals. $^1$H NMR (acetone-d$_6$) δ5.22 (s, 3H), 6.91–7.42 (m, 4H), 8.22–9.05 (m, 12H), 8.95 (bs, 1H).

3'-Hydroxyphenyl 10-methylacridan-9-carboxylate (1c).

3'-Hydroxyphenyl-10-methyl acridinium-9-carboxylate trifluoromethanesulfonate (500 mg, 1 mmol) was suspended in absolute ethanol (70 mL) and refluxed for 30 min. Ammonium chloride (5.6 g, 0.104 mol) was added by portions to the heterogeneous mixture followed by zinc (6.8 g, 0.104 mol). The yellow color of the solution disappeared immediately after the addition of zinc. The colorless solution was refluxed for 3 h. TLC of the reaction mixture showed complete conversion to a nonpolar material. The reaction mixture was filtered and the precipitate was washed with ethanol (3×30 mL). The filtrate was concentrated to obtain an off-white solid which was redissolved in methylene chloride and washed with water (2×30 mL). The organic layer was dried over Na$_2$SO$_4$ and concentrated to yield the product as an off-white solid. $^1$H NMR (CDCl$_3$) δ3.42 (s, 3H), 4.85 (s, 1H), 5.17 (s, 1H), 6.37–7.37 (m, 12H).

4. Synthesis of Acridan Derivative 1d 6-(tert-Butyldimethylsilyloxy)-2-naphthol, To a solution of 2,6-dihydroxynaphthalene (1.4 g, 8.7 mmol) and tert-butyldimethylsilyl chloride (1.31 g, 8.7 mmol) in 5 mL of dry DMF was gradually added imidazole (1.2 g, 17 mmol) and the solution was stirred for 1 hr. The solution was poured into 25 mL of water and extracted with 3×25 mL of ether. The combined ether solutions were dried over anhydrous MgSO$_4$. Evaporation of solvent gave a solid which was dissolved in hexane and filtered to remove unreacted starting material. Crude material was chromatographed on silica using 20% ethyl acetate/hexane to give the product as a white solid in 75% yield: $^1$H NMR (CDCl$_3$) δ0.219 (s, 6H), 1.002 (s, 9H), 4.81 (s, 1H), 7.01–7.60 (m, 6H); $^{13}$C NMR (CDCl$_3$) δ–4.17, 18.42, 25.92, 109.92, 115.28, 118.32, 122.80, 127.91, 128.62, 130.04, 130.38, 151.77, 151.92.

6'-(tert-Butyldimethylsilyloxy)acridine-9-carboxylate.

Acridine-9-carboxylic acid (500 mg, 2.2 mmol) was suspended in thionyl chloride (5 mL) and the reaction mixture was refluxed for 3 hr. The solvent was removed under reduced pressure to obtain a yellow solid which was dissolved in methylene chloride and pyridine (100 μL) under argon. This solution was cooled in an ice bath and a solution of 6-(tert-butyldimethylsilyloxy)-2-naphthol (735, mg, 2.6 mmol) in methylene chloride was added dropwise. The reaction mixture was stirred overnight at room temperature. The solution was concentrated to obtain a solid which was dissolved in ethyl acetate and washed with water. The organic layer was dried over $MgSO_4$ and concentrated to obtain a crude material which was chromatographed on silica gel (25% ethyl acetate/hexane) to yield the pure product as a yellow solid (65%). $^1$H NMR ($CDCl_3$) δ0.278 (s, 6H), 1.044 (s, 9H), 7.16–8.34 (m, 14H); $^{13}$C NMR ($CDCl_3$) δ –4.25, 18.34, 25.78, 115.14, 118.47, 120.95, 122.49, 123.33, 124.98, 127.56, 128.58, 129.22, 129.40, 130.17, 133.15, 135.97, 146.62, 148.75, 153.92, 166.32

6'-Hydroxynaphthyl 10-methylacridinium-9-carboxylate trifluoromethanesulfonate.

6-(tertbutyldimethylsilyloxy)naphthyl acridine-9-carboxylate (500 mg, 1 mmol) was dissolved in methylene chloride (5 ml) under argon and methyl trifluoromethanesulfonate (1.2 mL, 10 mmol) was added. A dark orange solution formed. The solution was stirred overnight at room temperature to yield a thick yellow precipitate. This precipitate was filtered, washed with ether and dried to obtain the product as orange crystals. $^1$H NMR (acetone-$d_6$) δ5.25 (s, 3H), 7.27–9.09 (m, 15H), 8.90 (s, 1H).

6'-Hydroxynaphthyl 10-methylacridan-9-carboxylate (1d).

6'-Hydroxynaphthyl-10-methyl acridinium-9-carboxylate trifluoromethanesulfonate (350 mg, 0.66 mmol) was suspended in absolute ethanol (30 mL) and refluxed for 15 min. Ammonium chloride (3.5 g, 66 mmol) was added by portions to the mixture followed by zinc (4.3 g, 66 mmol). The yellow color of the solution disappeared immediately after the addition of zinc. The colorless solution was refluxed for 4 hr. TLC of the reaction mixture showed complete conversion to a non-polar material. The solution was filtered and the precipitate was washed with ethanol (3×30 mL). Ethanol was evaporated to obtain an off-white solid which was redissolved in ethyl acetate and washed with water (2×30 mL). The organic layer was dried over $Na_2SO_4$ and concentrated to yield the crude product which was chromatographed on silica gel (30% ethyl acetate/hexane) to yield the pure product as an off-white solid. $^1$H NMR (acetone-$d_6$) δ3.38 (s, 3H), 5.34 (s, 1H), 6.94–7.70 (m, 14H), 8.70 (bs, 1H); $^{13}$C NMR ($CDCl_3$) δ33.53, 50.02, 118.97, 120.02, 121.46, 122.09, 128.21, 129.35, 129.95, 130.79, 133.79, 143.36, 147.56, 156.11, 171.05.

5. Synthesis of Acridan Derivative 1e

N-(Phenyl) p-toluenesulfonamide.

Aniline (1.86 g, 0.02 mol) was dissolved in methylene chloride under nitrogen and triethylamine (3.8 mL, 0.02 mol) was added. This solution was cooled in an ice bath and a solution of p-toluenesulfonyl chloride (3.8 g, 0.02 mol) was added dropwise via a syringe. After stirring this solution for 4 h at room temperature, TLC analysis (silica gel, 20% ethyl acetate/hexane) indicated completion of the reaction. The reaction mixture was poured into ether and the precipitate filtered. The ether layer was washed with water, dried over $MgSO_4$ and concentrated to yield an oily material. This crude product was chromatographed on silica using 35% ethyl acetate and hexane to obtain a solid which was further recrystallized in methylene chloride/hexane; m.p. 104° C.; $^1$H NMR ($CDCl_3$) δ2.36 (s, 3H), 7.07–7.25 (m, 8H), 7.67–7.69 (d, 2H).

N-(Phenyl)-N-(p-toluenesulfonamido) acridine-9-carboxamide.

N-Phenyl p-toluene-sulfonamide (247 mg, 1 mmol) was dissolved in toluene and treated with potassium tert-butoxide (112 mg, 1 mmol) under argon. After stirring the solution for 30 min, solvent was removed under reduced pressure to obtain a white solid. The potassium salt was resuspended in anhydrous tetrahydrofuran under argon and a solution of acridine-9-carboxylic acid chloride [obtained by refluxing acridine-9-carboxylic acid (156 mg, 0.75 mmol) and thionyl chloride (3 mL)] in methylene chloride was added. Triethylamine was added and reaction mixture was stirred at room temperature overnight. After evaporation of solvent, the residue was redissolved in ethyl acetate and washed with water. Organic layer was dried over $MgSO_4$ and concentrated to obtain a crude material which was chromatographed on silica gel (30% ethyl acetate/hexane) to yield the pure product as an off-white solid. $^1$H NMR ($CDCl_3$) δ2.57 (s, 3H), 6.85–7.03 (m, 5H), 7.51–8.09 (m, 12H).

10-Methyl-N-(phenyl)-N-(p-toluenesulfonamido) acridinium-9-carboxamide trifluoromethanesulfonate.

N-Phenyl-N-(p-toluenesulfonamido)acridine-9-carboxamide (30 mg, 0.0068 mmol) was dissolved in methylene chloride (5 mL) under argon and methyl trifluoromethanesulfonate (77 μL, 0.068 mmol) was added. The solution was stirred overnight at room temperature to yield a yellow precipitate. Hexane was added and the precipitate filtered. Solid was further washed with ether and dried to obtain the product as yellow crystals. $^1$H NMR (acetone-$d_6$) δ2.58 (s, 3H), 5.02 (s, 3H), 7.02–8.79 (m, 12H).

10-Methyl-N-(phenyl)-N-(p-toluenesulfonamido) acridan-9-carboxamide (1e).

10-Methyl-N-(phenyl)-N-(p-toluenesulfonamido)acridinium-9-carboxamide trifluoromethanesulfonate (10 mg, 0.0016 mmol) was suspended in absolute ethanol (10 mL) and solution was refluxed for 15 min to obtain a clear solution. Ammonium chloride (88 mg, 1.6 mmol) was added by portions to the solution followed by zinc (108 mg, 1.6 mmol). The yellow color of solution disappeared immediately after the addition of zinc. Colorless solution was refluxed for 2 h. TLC of reaction mixture showed complete conversion to a non-polar material. Solution was filtered and precipitate was washed with ethanol (3×20 mL). Solution was concentrated to obtain an off-white solid which was redissolved in methylene chloride and washed with water (2×15 mL). Organic layer was dried over $Na_2SO_4$ and concentrated to yield the crude product which was purified by preparative TLC using (30% ethyl acetate:hexane) Pure product was obtained as an off-white solid. $^1$HNMR ($CDCl_3$) δ2.40 (s, 3H), 3.18 (s, 3H) 5.00 (s, 1H), 6.76–7.77 (m, 12H).

Chemiluminescence Measurements

The experiments in the following examples were performed using a Turner Designs TD-20e luminometer fitted with neutral density filter for light attenuation. Data collection, analysis and display were software controlled. Constant temperature was maintained by means of an external circulating water bath connected to the luminometer.

6. Comparison of Compounds 1a–e at pH 8.9, Time Course and Total Intensity

Figure 1:
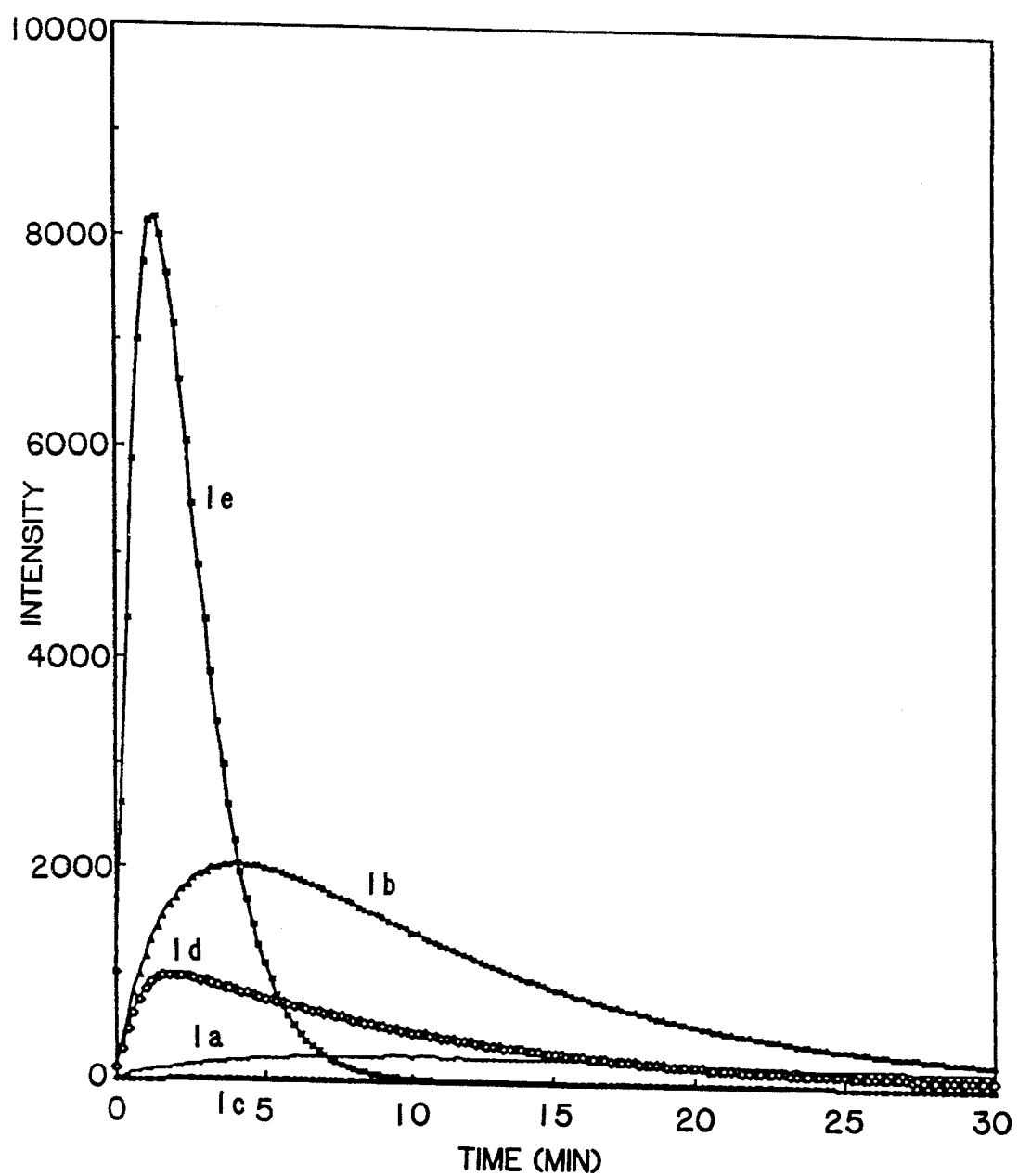
FIG. 1 is a graph showing a comparison of the light emission profiles from a series of five acridan compounds of the present invention. A 200 µL volume of a reagent composition containing 0.1 mM acridan compound 1a–e in 0.1M phosphate buffer, pH 8.9, 0.015% (6.2 mM) $H_2O_2$, 2.25 mM p-iodophenol, 0.5% (w/w) Tween 20 and 1 mM EDTA was reacted with $1 \times 10^{-13}$ mol of horseradish peroxidase.

A 200 μL volume of a formulation containing 0.01 mM acridan compound 1a–e in 0.1M phosphate buffer, pH 8.9, 0.015% (6.2 mM) $H_2O_2$, 2.25 mM p-iodophenol, 0.5% (w/w) Tween 20 and 1 mM EDTA was reacted with $1\times10^{-13}$ mol of horseradish peroxidase. FIG. 1 shows a comparison of the light emission profiles under these conditions. Compared below are the peak light intensity ($I_{max}$) in relative light units (RLU), the time to maximum light intensity ($t_{max}$) and total light output.

| Compound | I max (RLU) | t max (min) | I total (RLU) |
|---|---|---|---|
| 1a | 247 | 9.6 | ca. $6 \times 10^5$ |
| 1b | 2047 | 4.2 | $2 \times 10^6$ |
| 1c | 24 | 7.8 | $3.6 \times 10^4$ |
| 1d | 992 | 1.8 | $7.4 \times 10^5$ |
| 1e | 8160 | 1.4 | $1.5 \times 10^6$ |

1a. Phenyl 10-methylacridan-9-carboxylate.
1b. 4'-Hydroxyphenyl 10-methylacridan-9-carboxylate.
1c. 3'-Hydroxyphenyl 10-methylacridan-9-carboxylate.
1d. 6'-Hydroxynaphthyl 10-methylacridan-9-carboxylate.
1e. N-(phenyl)-N-(p-toluenesulfonamido) 10-methylacridan-9-carboxamide.

Compound 1b may be the best suited for various assay applications. The para-position of the OH group significantly increases the amount of light.

7. Sensitivity of Detection of Horseradish Peroxidase using 1b and Hydrogen Peroxide A matrix optimization experiment was done using 1b (0.1 mM–0.05 mM), hydrogen peroxide (4.4 mM–44 µM), HRP ($9\times10^{-19}$ mol–$1.4\times10^{-12}$ mol) at 37° C. The final assay reagent consists of $2.25\times10^{-3}$M p-iodophenol, 0.5% Tween 20 and $1\times10^{-3}$M EDTA in pH 8.0, 0.1M tris buffer. The best compromise between sensitivity and dynamic range was obtained using 1b (46 µmol/L) and 0.2 mmol/L hydrogen peroxide. These conditions gave a linear assay for HRP in the range of $9\times10^{-19}$ to $1.4\times10^{-14}$ mol (detection limit S/B=1.4 after 5 min with $9\times10^{-19}$ mol) or in the range of $9\times10^{-19}$ to $1.4\times10^{-15}$ mol (detection limit S/B=2 after 15 min with $9\times10^{-19}$ mol).

Figure 2A:
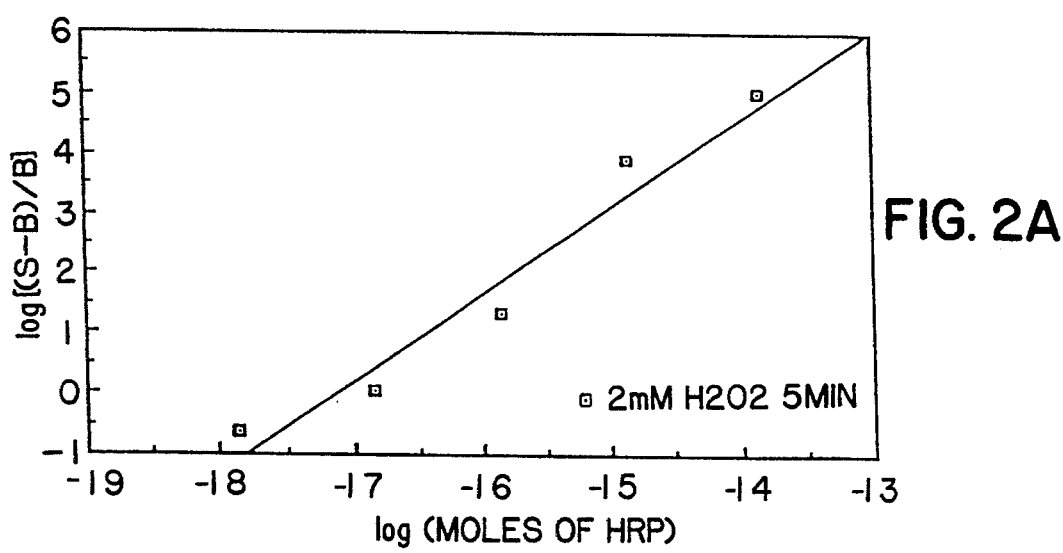
FIGS. 2A, 2B and 2C are a set of graphs showing the correlation of corrected signal to background vs. amount of HRP using solutions containing 0.05 mM 1b, 0.5% Tween 20, $1 \times 10^{-3}$M EDTA in pH 8.0, 0.1M tris buffer. The three graphs demonstrate the effect of $H_2O_2$ concentration and reaction time on sensitivity and linearity of detection.
Figure 2B:
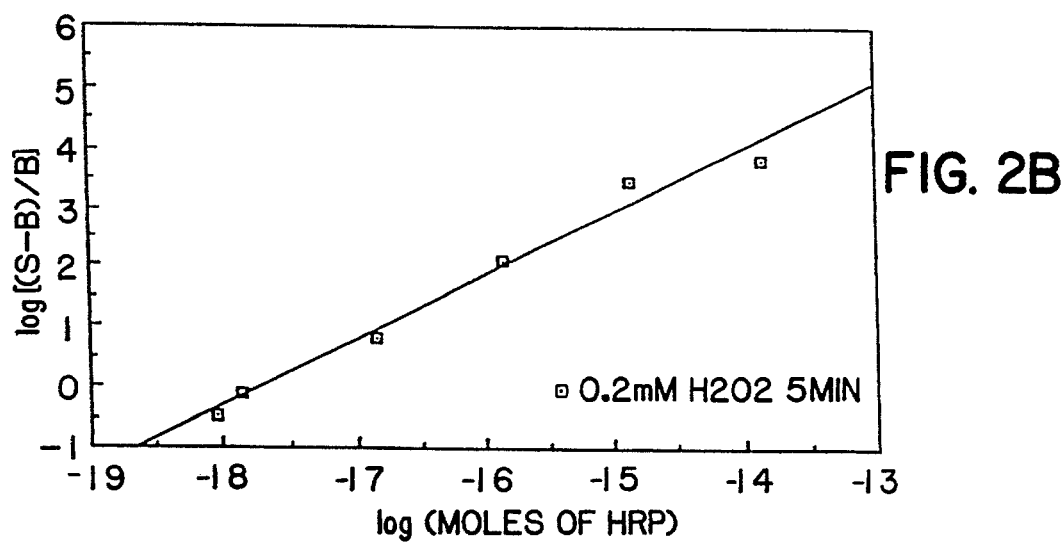
Figure 2C:
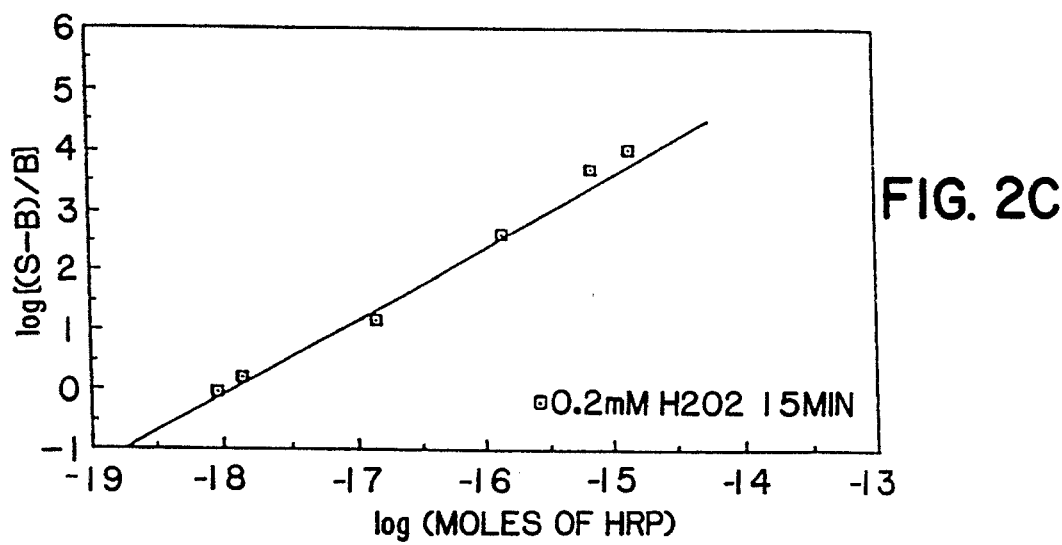

FIGS. 2A to 2C show the correlation of corrected signal to background vs. amount of HRP using solutions containing 0.05 mM 1b, 0.5% Tween 20, $1\times10^{-3}$M EDTA in pH 8.0, 0.1M tris buffer. Incubation times and [$H_2O_2$] are as shown in the Figures.

8. Sensitivity of Detection of Horseradish Peroxidase using 1b and Sodium Perborate A matrix optimization experiment was done using 1b (0.1 mM–0.05 mM), sodium perborate (3 mM–0.2 mM) and HRP ($1.4\times10^{-18}$ mol–$1.4\times10^{-14}$ mol) at 37° C. The final assay reagent consists of $2.25\times10^{-3}$M p-iodophenol, 0.5% Tween 20 and $1\times10^{-3}$M EDTA in pH 8.0, 0.1M tris buffer. The best compromise between sensitivity and dynamic range was obtained using 1b (46 µmol/L) and 0.2 mmol/L perborate. These conditions gave a linear assay for HRP in the range of $0.4\times10^{-18}$ to $1.4\times10^{-14}$ mol (detection limit S/B=1.4 after 5 min with $1.4\times10^{-18}$ mol) or in the range of $1.4\times10^{-18}$ to $1.4\times10^{-15}$ mol (detection limit S/B–1.5 after 15 min with $1.4\times10^{-18}$ mol).

Figure 3A:
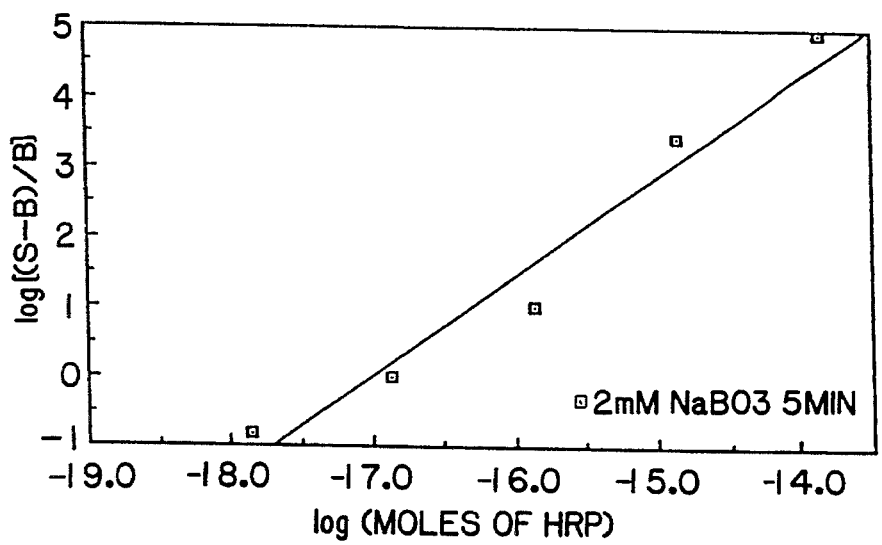
FIGS. 3A, 3B and 3C are a set of graphs showing the correlation of corrected signal to background vs. amount of HRP using solutions containing 0.05 mM 1b, 0.5% Tween 20, $1 \times 10^{-3}$M EDTA in pH 8.0, 0.1M tris buffer. The three graphs demonstrate the effect of $NaBO_3$ concentration and reaction time on sensitivity and linearity of detection.
Figure 3B:
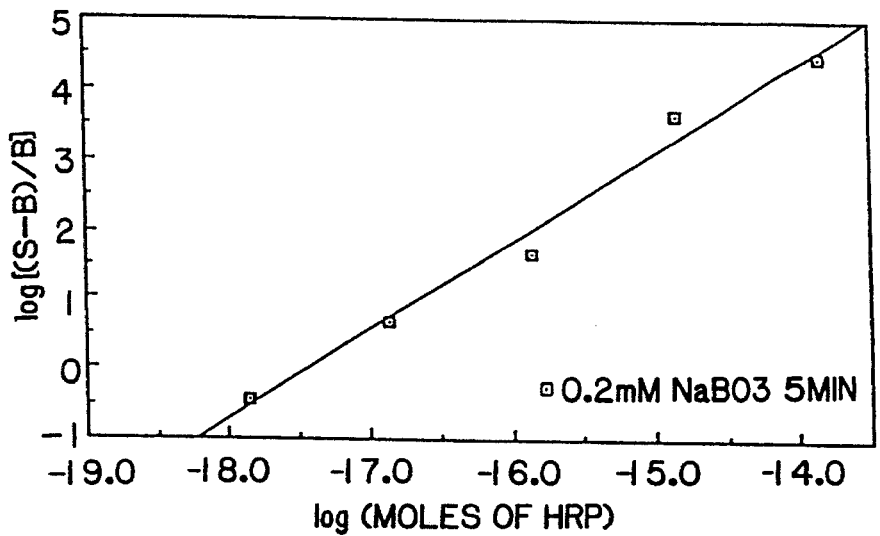
Figure 3C:
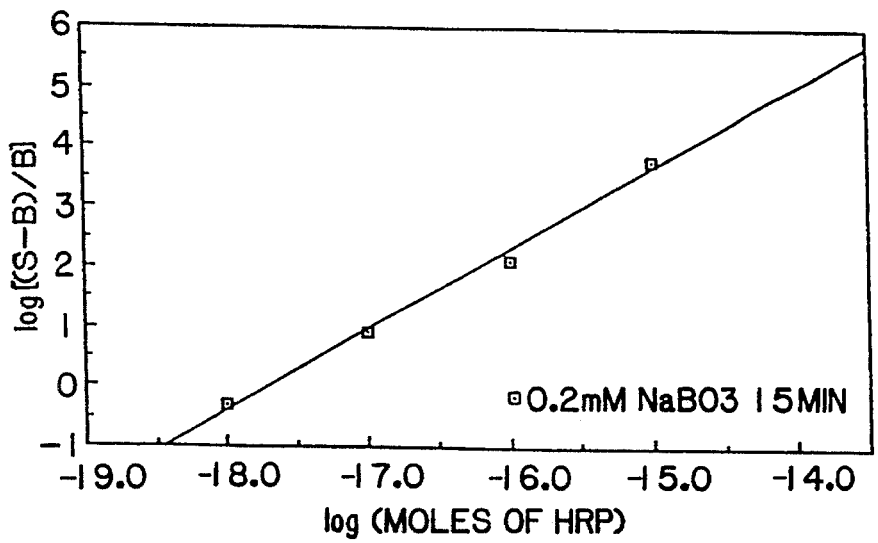

FIGS. 3A to 3C show the correlation of corrected signal to background vs. amount of HRP using solutions containing 0.05 mM 1b, 0.5% Tween 20, $1\times10^{-3}$ M EDTA in pH 8.0, 0.1M tris buffer. Incubation times and [$NaBO_3$] are as shown in the Figures.

9. Effect of pH and Buffer Salt

The present invention may be practiced over the pH range of at least 7–9 and functions with different buffering salts. Tubes containing 200 µL of a formulation containing 0.1 mM 1b in the specified buffer, 0.8 mM $H_2O_2$, 2.25 mM p-iodophenol, 0.5% (w/w) Tween 20 and 1 mM EDTA were placed in the luminometer at room temperature. Horseradish peroxidase ($1.4\times10^{-15}$ mol) was injected and the chemiluminescence intensity determined at 30 min. The time course of the light emission was similar in all four solutions. The optimum pH can vary with changes in the concentrations of the reactants.

| Buffer | S/B |
|---|---|
| 0.1 M tris buffer, pH 8.0 | 1400 |
| 0.1 M tris buffer, pH 8.5 | 600 |
| 0.1 M tris buffer, pH 8.9 | 160 |
| 0.1 M phosphate buffer, pH 8.9 | 306 |

10. Optimization of Enhancer and Peroxide Concentration

Enhancement of light emission from the HRP-catalyzed oxidation of 1b was studied using p-iodophenol. A series of concentrations of p-iodophenol (0.23 mM–4.5 mM) was used in 0.1M tris buffer, pH 8.0. Signal to background ratios obtained after incubation with $7\times10^{-16}$ mol of HRP for 15 min were compared using different assay reagents 1b (0.1 mM– 0.05 mM) and peroxide (0.2 mM–0.8 mM)]. The best compromise between sensitivity and concentration was obtained using 1.1 mMp-iodophenol with 0.8 mMperoxide and 0.05 mM 1b. At the best level, 2500-fold enhancement in chemiluminescence intensity (compared to an identical solution containing no enhancer) was obtained using p-iodophenol with $7\times10^{-16}$ mol of enzyme.

Figure 4:
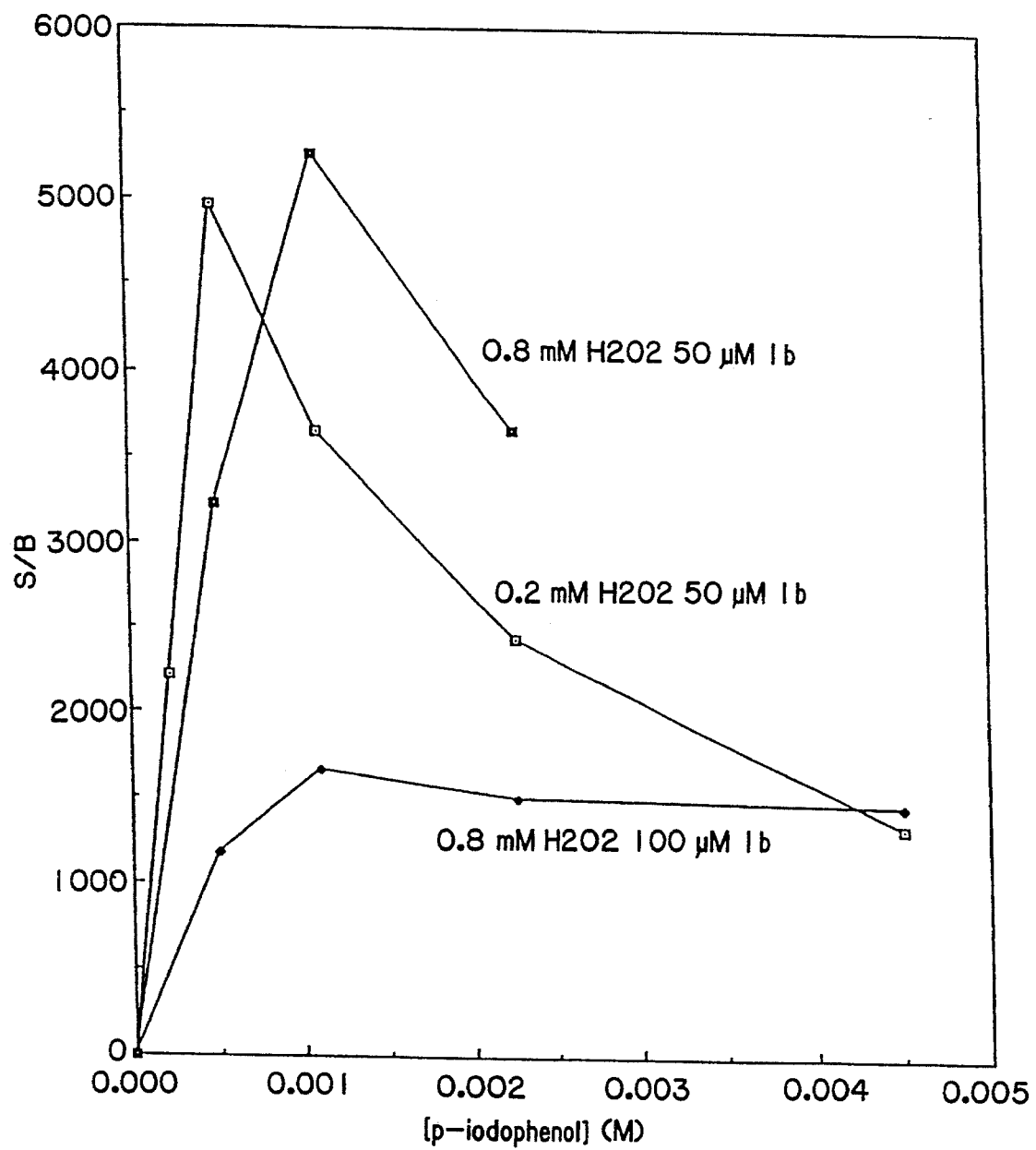
FIG. 4 is a graph showing the correlation of corrected signal to background vs. the amount of HRP using solutions containing p-iodophenol (0–4.5 mM), 0.5% Tween 20, $1 \times 10^{-3}$M EDTA in pH 8.0, 0.1M tris buffer and $7 \times 10^{-16}$ mol of HRP after a 15 min reaction time at 37° C. Concentrations of 1b and $H_2O_2$ are as stated in FIG. 4.

FIG. 4 shows the correlation of corrected signal to background vs. amount of HRP using solutions containing p-iodophenol (0–4.5 mM), 0.5% Tween 20, $1\times 10^{-3}$M EDTA in pH 8.0, 0.1M tris buffer and $7\times10^{-16}$ mol of HRP after a 15 min reaction time at 37° C. Concentrations of 1b and $H_2O_2$ are as shown in the Figure.

11. Improvement of Detection by Phenol Enhancers

To 220 µL of a formulation containing 0.1 mM 1b, 2.25 mM enhancer, 0.8 mM $H_2O_2$, 0.5% (w/w) Tween 20 and 1 mM EDTA in 0.1M tris buffer, pH 8.5 at 25° C. an aliquot containing $1\times10^{-15}$ mol of HRP was injected and the chemiluminescence at 30 min was measured. Table II below indicates that using p-iodophenol produced the maximum signal while slightly lower enhancement factors were observed with 2.25 mMp-phenylphenol and 2-naphthol while very little enhancement was obtained with p-hydroxycinnamic acid at this concentration. The absolute and relative enhancement factors obtained for a given enhancer are dependent on the concentrations of enhancer, peroxide and enzyme. For example, separate optimization of p-hydroxycinnamic acid concentration led to an improvement in enhancement factor.

TABLE II

| Enhancer | S/B |
|---|---|
| p-iodophenol | 600 |
| p-phenylphenol | 200 |
| 2-naphthol | 138 |
| p-hydroxycinnamic acid | 9 |

12. Improvement of Detection by Surfactants

It has been found that certain surfactants such as nonionic surfactants improve the utility of the present invention by providing a better signal to background ratio. The improvement occurs through minimizing the background chemiluminescence in the absence of added peroxidase, possibly due to a slowing of the autoxidative decomposition of the ester. In one experiment, Tween 20 (0.5%–1%) decreased the background luminescence from a solution of 1b by a factor of 65 compared to a similar solution lacking the surfactant. SDS (sodium dodecyl sulfate) similarly lowers background luminescence but is not preferred for use in solutions containing higher concentrations of enzyme.

13. Detection of HRP at 25° C. and 37° C.

Figure 5:
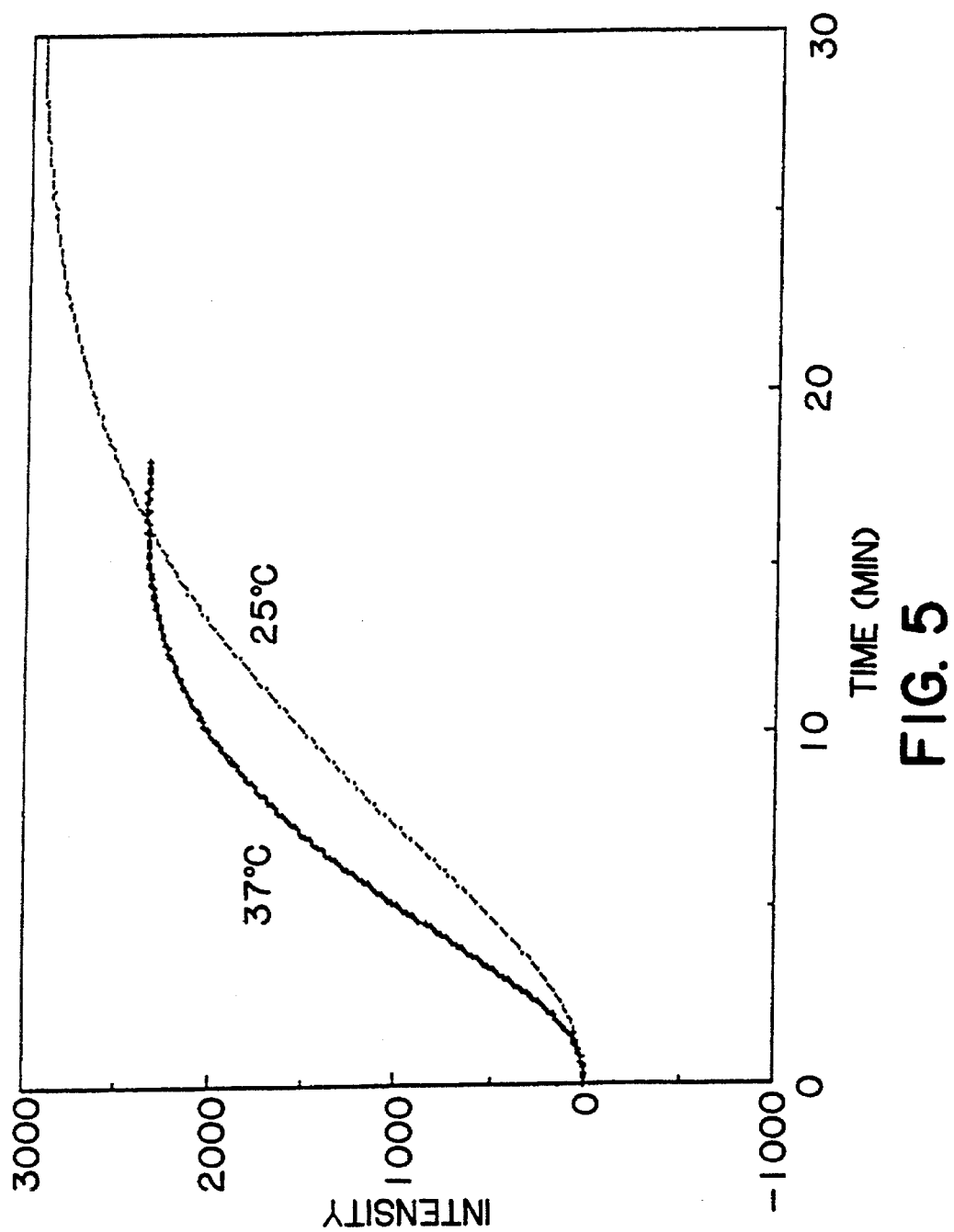
FIG. 5 is a graph showing the results at 25° C. and 37° C. Light intensity vs. time curves resulting from the treatment of 200 µL of a formulation containing 0.05 mM compound 1b, 0.2 mM $H_2O_2$, 0.5 mM p-iodophenol, 0.5% (w/w) Tween 20 and 1 mM EDTA in 0.1M tris buffer, pH 8.0 incubated at 25° C. or 37° C. with 10 µL of a solution containing $7 \times 10^{-16}$ mol of horseradish peroxidase are shown. The chemiluminescence intensity reaches a maximum faster at 37° C.

The present invention may be practiced over the temperature range of at least 25° C. to 37° C. Light intensity vs. time curves resulting from the treatment of 200 µL of a formulation containing 0.05 mM compound 1b, 0.2 mM $H_2O_2$, 0.5 mM p-iodophenyl, 0.5% (w/w) Tween 20 and 1 mM EDTA in 0.1M tris buffer, pH 8.0 incubated at 25° C. or 37° C. with ten µL of solution containing $7 \times 10^{-16}$ mol of horseradish peroxidase are shown in FIG. 5. The chemiluminescence intensity reaches a maximum faster at 37° C.

14. Comparison of Detection of HRP with Luminol and 1b

Figure 6:
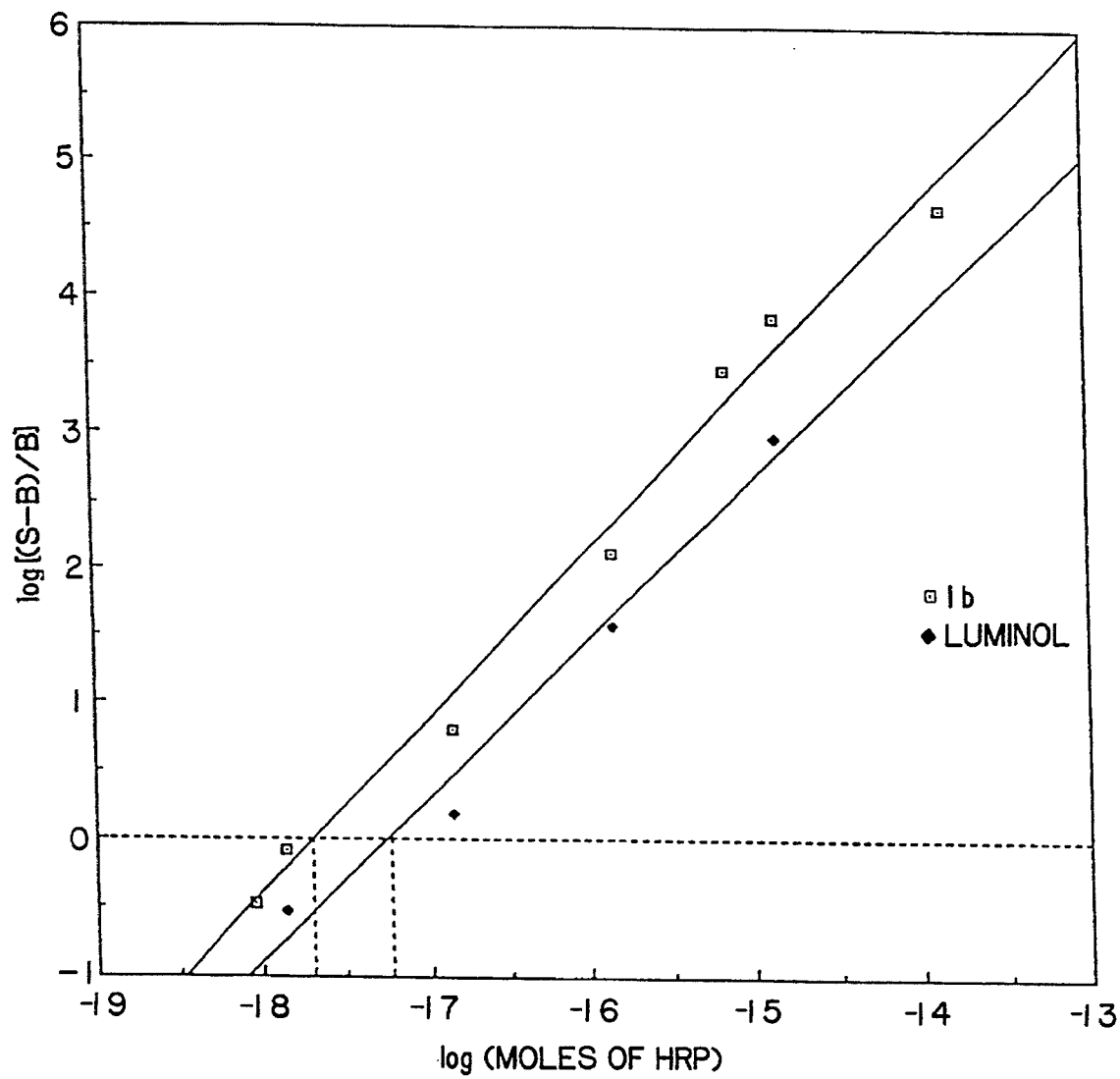
FIG. 6 is a log-log graph showing the linearity of detection of HRP using a reagent composition of the present invention as compared to a commercially available optimized reagent containing luminol. The reagent of the present invention comprises 40 µL of a solution containing 1b (0.05 mM), p-iodophenol (2.25 mM), H₂O₂ (0.2 mM), Tween 20 (0.5%), EDTA (1 mM) in 0.1M tris, pH 8.0. For comparison, 40 μL of the acridan reagent and the luminol reagent were separately incubated at 37° C. and reacted with varying amounts of HRP. The graph compares the corrected signal-to-background ratios at 5 min. The reagent containing 1b is capable of greater sensitivity of detection (comparing log (S-B)/B=O) than the luminol reagent. This improved sensitivity is evident by comparing log (moles HRP) for each reagent at the same value of zero for log [(S-B)/B].

As shown in FIG. 6, the linearity of detection of HRP using a reagent composition of the present invention was compared to a commercially available optimized reagent containing luminol. Forty µL of a solution containing 1b (0.05 mM), p-iodophenol (2.25 mM), $H_2O_2$ (0.2 mM), Tween 20 (0.5%), EDTA (1 mM) in 0.1M tris, pH 8.0 and forty µL of the commercial reagent (Amersham, Arlington Heights, Ill.) were incubated at 37° C. and reacted with varying amounts of HRP. FIG. 6 compares the corrected signal-to-background ratios at 5 min. The reagent containing 1b is capable of greater sensitivity of detection (comparing log S-B)/B=0) than the luminol reagent. Measuring light intensity at 15 min provides an additional reduction in detection limit with the reagent containing 1b, while the luminol reagent results are unchanged.

15. Chemiluminescent Detection of Proteins by Western Blot

To determine the sensitivity of reagents of the present invention for detection of proteins by Western blotting, a model system of transferrin was used to provide polypeptide bands in known quantities.

Rabbit anti-goat IgG-peroxidase conjugate and rabbit anti-goat IgG-peroxidase were obtained from Cappel Products (Durham, N.C.). Human transferrin and fractionated goat anti-human transferrin serum were purchased from Sigma Chemical Co. (St. Louis, Mo.)). The IgG sample was centrifuged at 10,000 g for two minutes and the supernatant was used in the immunological reaction. Immobilon™-P transfer membrane was obtained from Millipore Corp. (Bedford, Mass.). Kodak (Rochester, N.Y.) X-OMAT AR and OMC films were used in the assay procedure.

SDS-PAGE was performed utilizing the buffer system described by Laemmli (U. K. Laemmli, Nature (London), 227, 680 (1970)). The stacking gel was 4.38% acrylamide: 0.12% bisacrylamide. The separating gel was 6.81% acrylamide: 0.19% bisacrylamide. Following electrophoresis the gel was equilibrated for 7–8 minutes with the transfer buffer which contained 20 mM Tris, 153 mMglycine and 20% (v/v) methanol. The gel, sandwiched between a sheet of transfer membrane and a sheet of chromatography paper 3MM (Whatman), was placed in the transfer unit (Bio-Rad Laboratories, Richmond, Calif.). The proteins in the gel were electroeluted for 50–60 min at 4° C. at a 100 V constant voltage. The membrane was then placed in 50 mM Tris-HCl buffered saline at pH 7.4 (TBS) at 4° C. overnight. After this period the membrane was washed with TBS for 15 min.

The membrane was treated with 0.05% Tween-20 in 50 mM Tris-HCl buffered saline at pH 7.4 (T-TBS) containing 1% non-fat powdered milk (NFM) for one hour at room temperature. This blocked membrane was incubated for 75 minutes at room temperature with primary antibody (1:500 dilution of goat anti-human transferrin IgG fraction) using T-TBS containing 1% NFM.

The membrane was then rinsed and washed three times for ten minutes each with T-TBS at room temperature. The washed membrane was incubated for one hour at room temperature with secondary antibody (1:25000 dilution of rabbit anti-goat IgG peroxidase conjugate) using T-TBS containing 1% NFM. The membrane was rinsed and washed four times for ten minutes each with T-TBS followed by a ten minute wash with TBS.

The washed membrane was soaked in a detection reagent solution containing a peroxide compound and 4'-hydroxyphenyl-10-methylacridan-9-carboxylate (1b) for ten minutes, drained, placed between sheets 0f transparency film. The X-ray film was exposed to the membrane for one to ten minutes and developed.

| Composition of detection reagent solution: | |
|---|---|
| Tris buffer, pH 8.8 | 0.1 M |
| 1b | $5 \times 10^{-5}$ M |
| p-iodophenol | $1.1 \times 10^{-4}$ M |
| Tween 20 | 0.5% (w/w) |
| $NaBO_3 \cdot 4H_2O$ | $1.6 \times 10^{-3}$ M |
| EDTA | $5 \times 10^{-4}$ M |

The transferrin standards utilized were clearly visible down to 20 pg/slot without background after a 7 sec. HAT exposure Kodak X-OMAT AR x-ray film (FIG. 7A) or after a 30 HAT second exposure to OMC x-ray film (FIG. 7B). It was possible to make several exposures of the membrane during the first hour as the membrane continued to emit light.

A significant advantage of detection reagents for HRP-conjugates on membranes containing N-alkylacridan carboxyl derivatives is the extended duration of light emission. In the present example, chemiluminescence can be detected by X-ray film for at least three hours, making optimization of exposure very convenient. Chemiluminescence emission can be extended by several hours by increasing the concentration of acridan 1b. In contrast, the best commercial chemiluminescent reagent for HRP detection only produces sufficient signal on membrane for about one hour.

It is intended that the foregoing description be only illustrative of the present invention and that the present invention be limited only by the hereinafter appended claims.

We claim:

1. An acridan of the formula

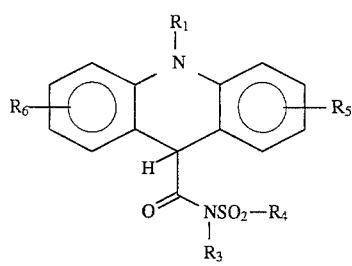

wherein $R_1$ is selected from the group consisting of alkyl, heteroalkyl and aralkyl groups, wherein $R_3$ and $R_4$ are selected from the group consisting of substituted and unsubstituted aryl groups and alkyl, heteroalkyl and aralkyl groups and wherein $R_5$ and $R_6$ are selected from the group consisting of hydrogen and non-interfering substituents and wherein

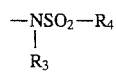

is a leaving group which allows the production of light from the acridan by reaction with a peroxide and a peroxidase.

2. The acridan of claim 1 wherein the acridan is of the formula

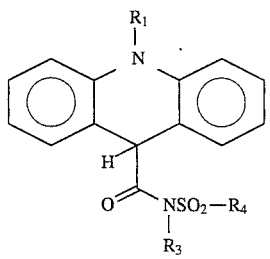

and wherein $R_3$ and $R_4$ are selected from the group consisting of substituted and unsubstituted aryl groups and alkyl, heteroalkyl and aralkyl groups.

3. The acridan of claim 2 wherein $R_3$ and $R_4$ are selected from the group consisting of substituted and unsubstituted phenyl and naphthyl groups.

4. The acridan of the formula

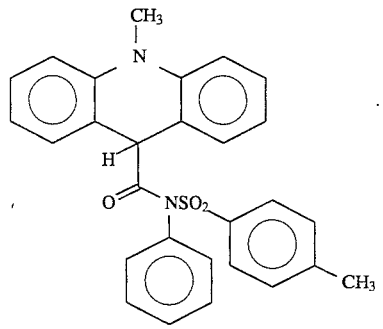

5. A method for producing chemiluminescence which comprises reacting a peroxide compound and a peroxidase with an acridan of the formula

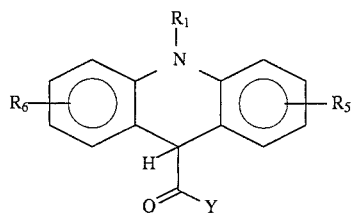

wherein $R_1$ is selected from the group consisting of alkyl, heteroalkyl and aralkyl groups, wherein $R_5$ and $R_6$ are selected from the group consisting of hydrogen and non-interfering substituents, wherein Y is a leaving group which allows the production of light from the acridan by reaction with a peroxide and a peroxidase.

6. The method of claim 5 wherein the leaving group Y is an $R_2$-oxy group ($R_2$-O) and wherein $R_2$ is selected from the group consisting of substituted and unsubstituted aryl groups.

7. The method of claim 6 wherein the $R_2$ group is selected from the group consisting of substituted and unsubstituted phenyl and naphthyl groups.

8. The method of claim 7 wherein the $R_2$ group is selected from the group consisting of hydroxyphenyl and hydroxynaphthyl groups.

9. The method of claim 5 wherein the acridan is of the formula

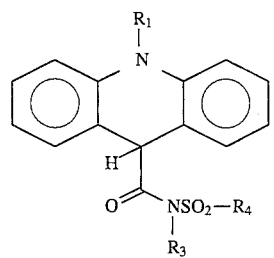

and wherein $R_3$ and $R_4$ are selected from the group consisting of substituted and unsubstituted aryl groups and alkyl, heteroalkyl and aralkyl groups.

10. The method of claim 9 wherein $R_3$ and $R_4$ are selected from the group consisting of substituted and unsubstituted phenyl and naphthyl groups.

11. The method of claim 5 wherein the acridan is selected from the group consisting of

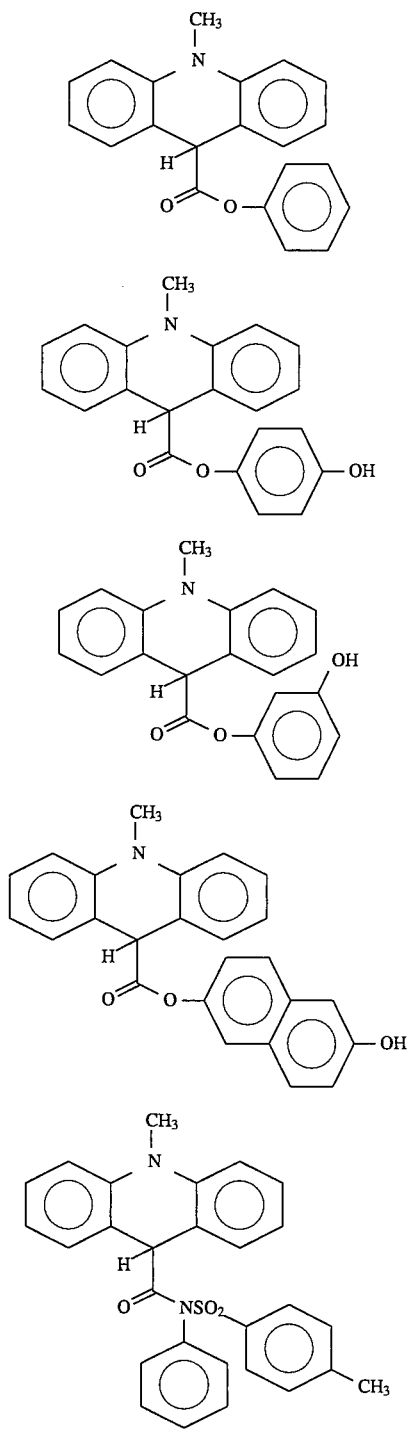

12. A reagent composition which generates light in the presence of a peroxidase which comprises:

(a) an acridan of the formula:

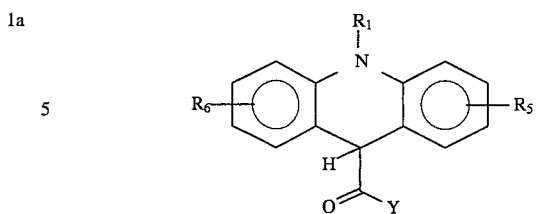

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase;

(b) optionally a phenolic compound which enhances light production from the acridan;

(c) a peroxide compound which participates in the reaction of the acridan with the peroxidase;

(d) a chelating agent which prevents the peroxide compound from reacting prior to addition of the peroxidase to the composition; and (e) a non-ionic surfactant.

13. The reagent composition of claim 12 wherein the leaving group Y is an $R_2$-oxy group ($R_2$-O) and wherein $R_2$ is selected from the group consisting of substituted and unsubstituted aryl groups.

14. The reagent composition of claim 13 wherein the $R_2$ group is selected from the group consisting of substituted and unsubstituted phenyl and naphthyl groups.

15. The reagent composition of claim 13 wherein the $R_2$ group is selected from the group consisting of hydroxyphenyl and hydroxynaphthyl groups.

16. The reagent composition of claim 12 wherein the acridan is of the formula $$\text{(structure with } R_1, \text{ NSO}_2\text{-}R_4, R_3\text{)}$$

and wherein $R_3$ and $R_4$ are selected from the group consisting of substituted and unsubstituted aryl groups and alkyl, heteroalkyl and aralkyl groups.

17. The reagent composition of claim 12 wherein $R_3$ and $R_4$ are selected from the group consisting of substituted and unsubstituted phenyl and naphthyl groups.

18. A reagent composition which generates light in the presence of a peroxidase which comprises:

(a) an acridan having a formula selected from the group consisting of:

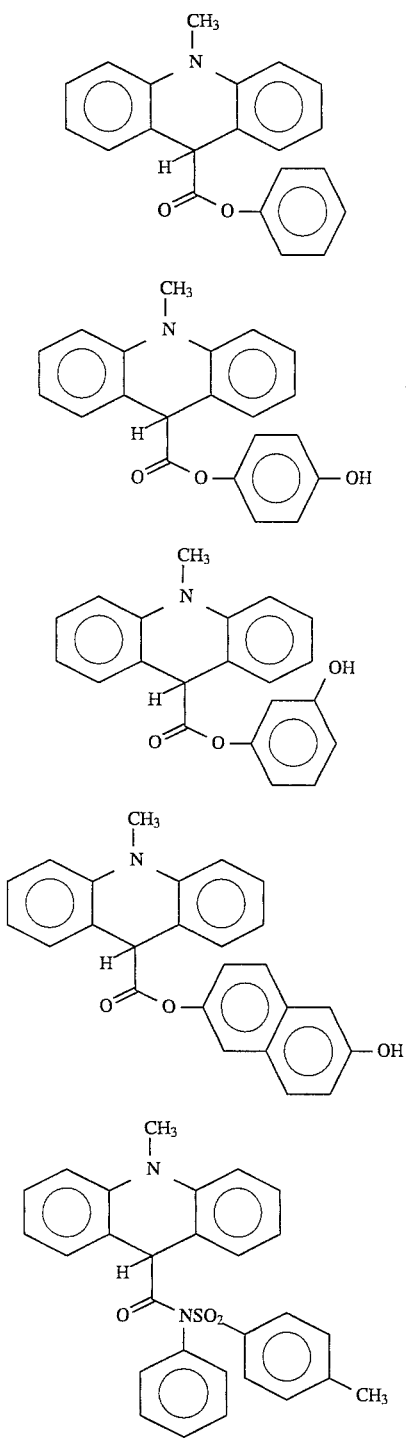

(b) optionally, a phenolic compound which enhances light production from the acridan;

(c) a peroxide compound which participates in the reaction of the acridan with the peroxidase;

(d) a chelating agent which prevents the peroxide compound from reacting prior to addition of the peroxidase to the composition; and (e) a non-ionic surfactant.

19. The reagent composition of any one of claims 12 or 18 wherein the chelating agent is ethylenediamine tetraacetic acid salt (EDTA).

20. The reagent composition of any one of claims 12 or 18 wherein the chelating agent is EDTA and wherein the phenolic compound is selected from the group consisting of p-phenylphenol, p-iodophenol, p-bromophenol, p-hydroxycinnamic acid, 2-cyano-6-hydroxybenzothiazole and 2-naphthol.

21. The reagent composition of any one of claims 12 or 18 wherein the molar ratio of phenolic compound to acridan is between about 0.001 and 100.

22. A method for detecting an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction comprising reacting an acridan with a peroxide and a peroxidase to produce light for detecting the analyte wherein the acridan is of the following formula

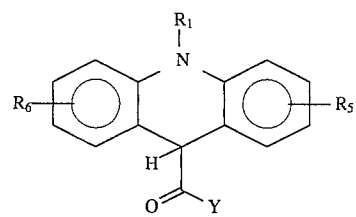

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with the peroxide and the peroxidase to detect the analyte.

23. The method of claim 22 wherein the leaving group Y is an $R_2$-oxy group ($R_2$-O) and wherein $R_2$ is selected from the group consisting of substituted and unsubstituted aryl groups.

24. The method of claim 23 wherein the $R_2$ group is selected from the group consisting of substituted and unsubstituted phenyl and naphthyl groups.

25. The method of claim 23 wherein the $R_2$ group is selected from the group consisting of hydroxyphenyl and hydroxynaphthyl groups.

26. The method of claim 22 wherein the acridan is of the formula

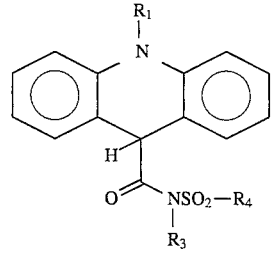

and wherein $R_3$ and $R_4$ are selected from the group consisting of substituted and unsubstituted aryl groups and alkyl, heteroalkyl and aralkyl groups.

27. The method of claim 22 wherein $R_3$ and $R_4$ are selected from the group consisting of substituted and unsubstituted phenyl and naphthyl groups.

28. The method of claim 22 wherein the acridan has the formula

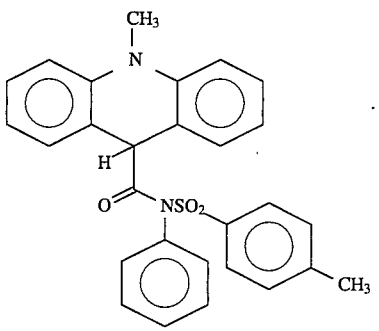

29. The method of claim 22 wherein the acridan has the formula

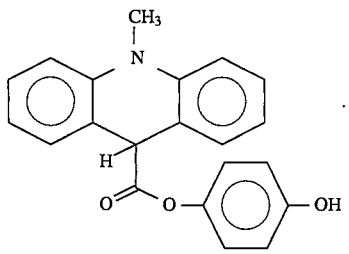

30. The method of claim 22 wherein the acridan has the formula:

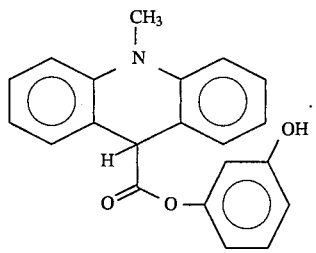

31. The method of claim 22 wherein the acridan has the formula:

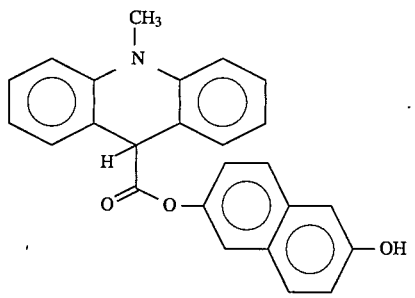

32. A method for detecting an analyte selected from the group consisting of peroxidase alone, organic molecules labeled with the peroxidase and biological molecules labeled with the peroxidase in an assay procedure by a chemiluminescent reaction comprising:

(a) providing a reagent composition which generates light in the presence of the peroxidase which comprises: an acridan of the formula:

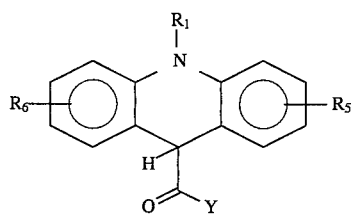

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase; optionally a phenolic compound which enhances light production from the acridan; a peroxide compound which participates in the reaction of the acridan with the peroxidase; a chelating agent which prevents the peroxide compound from reacting prior to the addition of the peroxidase to the composition; and a non-ionic surfactant; and (b) reacting the peroxidase with the reagent composition so that light is produced for detecting the analyte.

33. The method of claim 32 wherein the leaving group Y is an $R_2$-oxy group ($R_2$-O) and wherein $R_2$ is selected from the group consisting of substituted and unsubstituted aryl groups.

34. The method of claim 33 wherein the $R_2$ group is selected from the group consisting of substituted and unsubstituted phenyl and naphthyl groups.

35. The method of claim 33 wherein the $R_2$ group is selected from the group consisting of hydroxyphenyl and hydroxynaphthyl groups.

36. The method of claim 33 wherein the acridan has the formula:

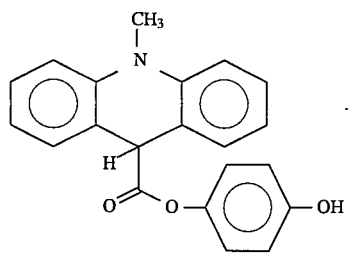

37. The method of claim 33 wherein the acridan has the formula:

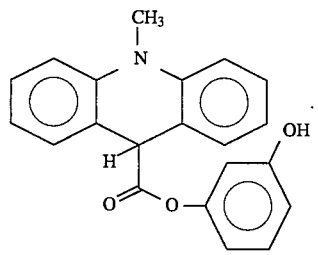

38. The method of claim 33 wherein the acridan has the formula:

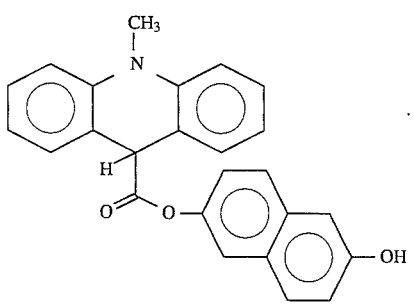

39. The method of claim 32 wherein the acridan is of the formula

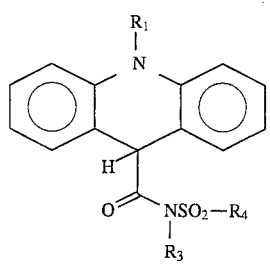

and wherein $R_3$ and $R_4$ are selected from the group consisting of substituted and unsubstituted aryl groups and alkyl, heteroalkyl and aralkyl groups.

40. The method of claim 39 wherein $R_3$ and $R_4$ are selected from the group consisting of substituted and unsubstituted phenyl and naphthyl groups.

41. The method of claim 39 wherein the acridan has the formula

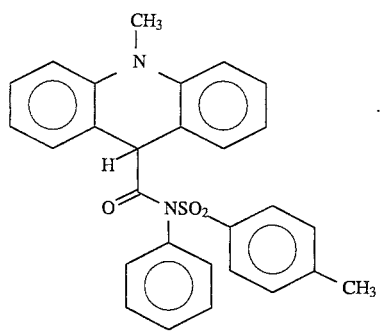

42. The method of claim 32, wherein the peroxidase enzyme is coupled to a compound which specifically binds to an analyte.

43. The method of claim 42 wherein the analyte-binding compound to which the peroxidase enzyme is coupled is selected from the group consisting of antibodies, oligonucleotides, haptens, and proteins.

44. The method of any one of claims 32, 33, 42 or 43 wherein the chelating agent in the reagent composition is EDTA.

45. The method of any one of claims 32, 33, 42 or 43 wherein the phenolic compound in the reagent composition is present in the composition and is selected from the group consisting of p-phenylphenol or p-iodophenol.

46. The method of any one of claims 32, 33, 42 or 43 wherein the phenolic compound in the reagent composition is selected from the group consisting of p-phenylphenol or p-iodophenol and the chelating agent is EDTA.

47. The method of any one of claims 32, 33, 42 or 43 wherein the detection is performed on a membrane.

48. The method of claim 47 wherein the membrane is selected from the group consisting of a nitrocellulose, nylon and polyvinylidene difluoride membranes.

49. The method of any one of claims 32, 33, 42 or 43 wherein the chemiluminescence produced is detected on photographic film.

50. The method of any one of claims 32, 33, 42, or 43 wherein the chemiluminescence produced is detected by a luminometer.

51. A kit for detecting in a sample an analyte selected from the group consisting of hydrogen peroxide, hydrogen peroxide generated by an enzyme, peroxidase alone, organic molecules labeled with the peroxidase and biological molecules labeled with the peroxidase in an assay procedure by a chemiluminescent reaction comprising reacting an acridan with a peroxide and a peroxidase to produce light which comprises in separate containers:

(a) an acridan of the formula:

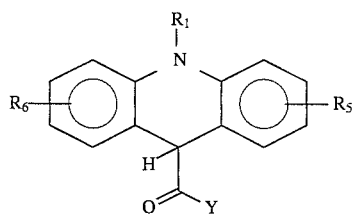

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase; and (b) a peroxidase, wherein the light is detected in the assay procedure by reacting the acridan with a peroxide, the peroxidase and the sample to thereby detect the analyte.

52. The kit of claim 51 wherein the leaving group Y is an $R_2$-oxy group ($R_2$-O) and wherein $R_2$ is selected from the group consisting of substituted and unsubstituted aryl groups.

53. The kit of claim 52 wherein the $R_2$ group is selected from the group consisting of substituted and unsubstituted phenyl and naphthyl groups.

54. The kit of claim 52 wherein the $R_2$ group is selected from the group consisting of hydroxyphenyl and hydroxynaphthyl groups.

55. The kit of claim 51 wherein the acridan is of the formula

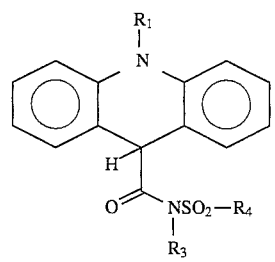

and wherein $R_3$ and $R_4$ are selected from the group consisting of substituted and unsubstituted aryl groups and alkyl, heteroalkyl and aralkyl groups.

56. The kit of claim 51 wherein $R_3$ and $R_4$ are selected from the group consisting of substituted and unsubstituted phenyl and naphthyl groups.

57. A kit for detecting in a sample an analyte selected from the group consisting of the hydrogen peroxide, hydrogen peroxide generated by an enzyme, peroxidase alone, organic molecules labeled with the peroxidase and biological molecules labeled with the peroxidase in an assay procedure by a chemiluminescent reaction comprising reacting an acridan with a peroxide and a peroxidase to produce light which comprises in separate containers:

(a) an acridan having a formula selected from the group consisting of:

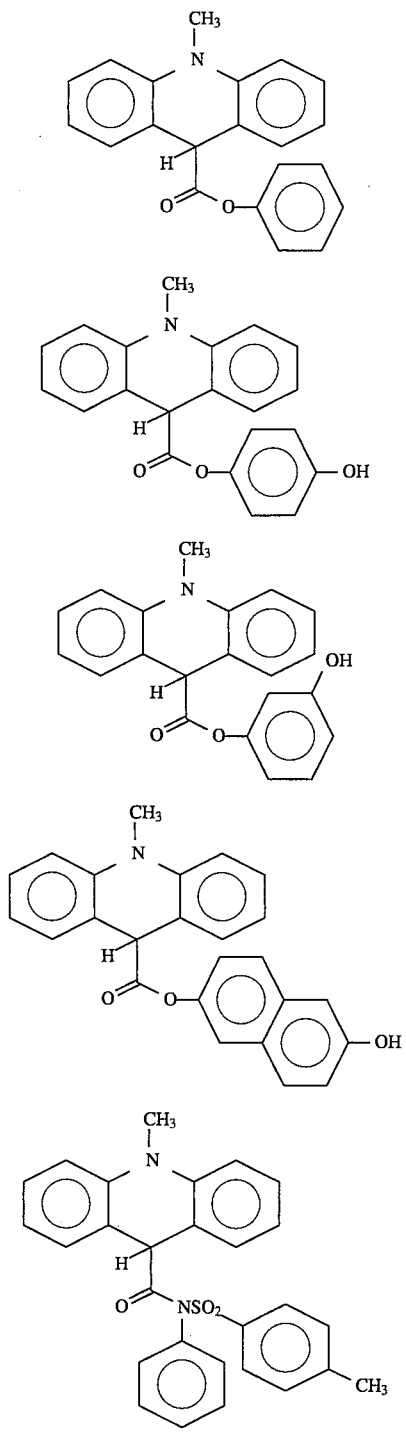

in a reagent composition; and (b) a peroxidase, wherein the light is detected in the assay procedure by reacting the acridan with the peroxide, the peroxidase and the sample to detect the analyte.

58. A kit for detecting in a sample an analyte selected from the group consisting of peroxidase alone, organic molecules labeled with the peroxidase and biological molecules labeled with the peroxidase in an assay procedure by a chemiluminescent reaction to produce light which comprises in separate containers:

(a) a reagent composition the components of which may be in a single or multiple containers which generates light in the presence of a peroxidase which comprises: an acridan of the formula:

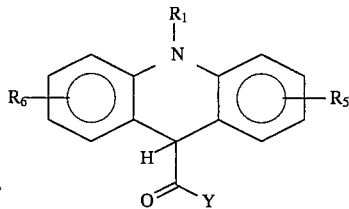

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with a peroxide and a peroxidase; optionally a phenolic compound which enhances light production from the acridan; a peroxide compound which participates in the reaction of the acridan with the peroxidase; a chelating agent which prevents the peroxide compound from reacting prior to the addition of a peroxidase to the composition; and a non-ionic surfactant; and (b) a peroxidase, wherein the light is detected in the assay procedure by reacting the reagent composition with the peroxidase and the sample to thereby detect the analyte.

59. The kit of claim 58 wherein the leaving group Y is an $R_2$-oxy group ($R_2$-O) and wherein $R_2$ is selected from substituted and unsubstituted aryl groups.

60. The kit of claim 59 wherein the $R_2$ group is selected from the group consisting of substituted and unsubstituted phenyl and naphthyl groups.

61. The kit of claim 60 wherein the $R_2$ group is selected from the group consisting of hydroxyphenyl and hydroxynaphthyl groups.

62. The kit of claim 58 wherein the acridan is of the formula

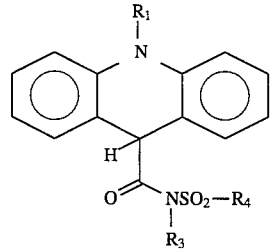

and wherein $R_3$ and $R_4$ are selected from the group consisting of substituted and unsubstituted aryl groups and alkyl, heteroalkyl and aralkyl groups.

63. The kit of claim 58 wherein $R_3$ and $R_4$ are selected from the group consisting of substituted and unsubstituted phenyl and naphthyl groups.

64. A kit for detecting in a sample an analyte selected from the group consisting of peroxidase alone, organic molecules labeled with the peroxidase and biological molecules labeled with the peroxidase in an assay procedure by a chemiluminescent reaction to produce light which comprised in separate containers:

(a) a reagent composition which may be in a single or multiple containers and which generates light in the presence of a peroxidase which comprises: an acridan selected from the group consisting of:

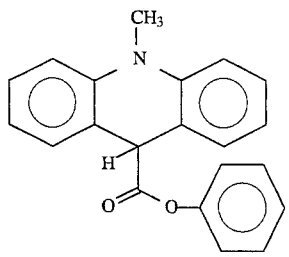

1a

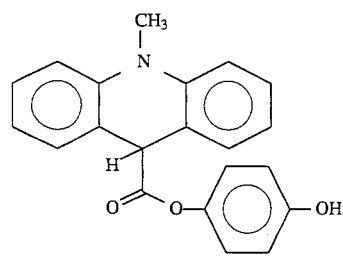

1b

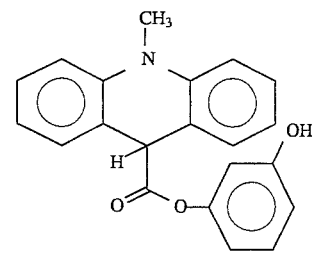

1c

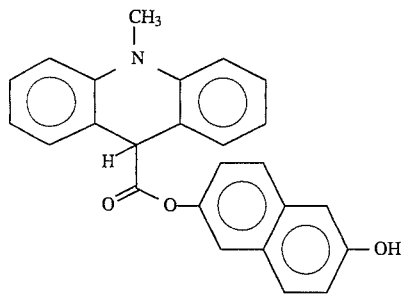

1d

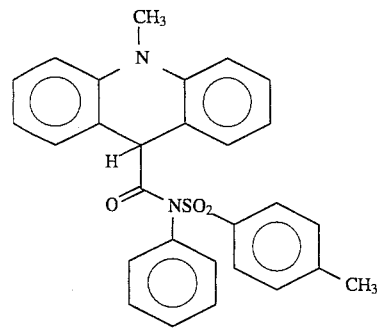

1e wherein $R_1$ is selected from the group consisting of alkyl, heteroalkyl and aralkyl groups, wherein $R_5$ and $R_6$ are selected from the group consisting or hydrogen and non-interfering substituents and wherein Y is a leaving group which allows the production of light from the acridan by reaction with a peroxide and a peroxidase; optionally a phenolic compound which enhances light production from the acridan; a peroxide compound which participates in the reaction of the acridan with the peroxidase; a chelating agent which prevents the peroxide compound from reacting prior to the addition of a peroxidase with the composition; and a nonionic surfactant; and (b) a peroxidase, wherein the light is detected in the assay procedure by reacting the reagent composition with the peroxidase and the sample to detect the analyte.

65. A method for detecting hydrogen peroxide in an assay procedure by a chemiluminescent reaction comprising reacting hydrogen peroxide and a peroxidase with an acridan of the formula:

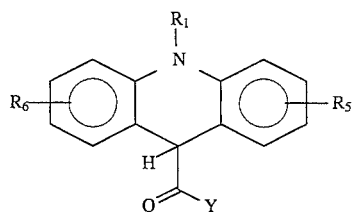

wherein $R_1$ is selected from the group consisting of alkyl, heteroalkyl and aralkyl groups, wherein $R_5$ and $R_6$ are selected from the group consisting of hydrogen and non-interfering substituents and wherein Y is a leaving group which allows the production of light from the acridan by reaction with the peroxide and the peroxidase to detect the hydrogen peroxide.

66. The method of claim 65 wherein the acridan is selected from the group consisting of:

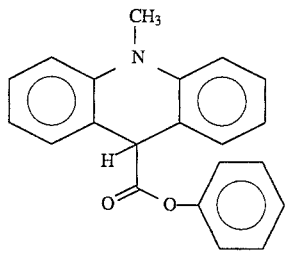

1a

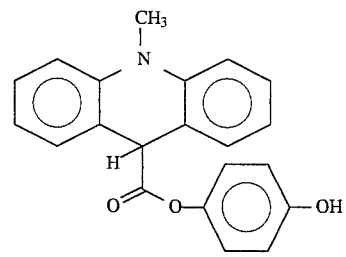

1b

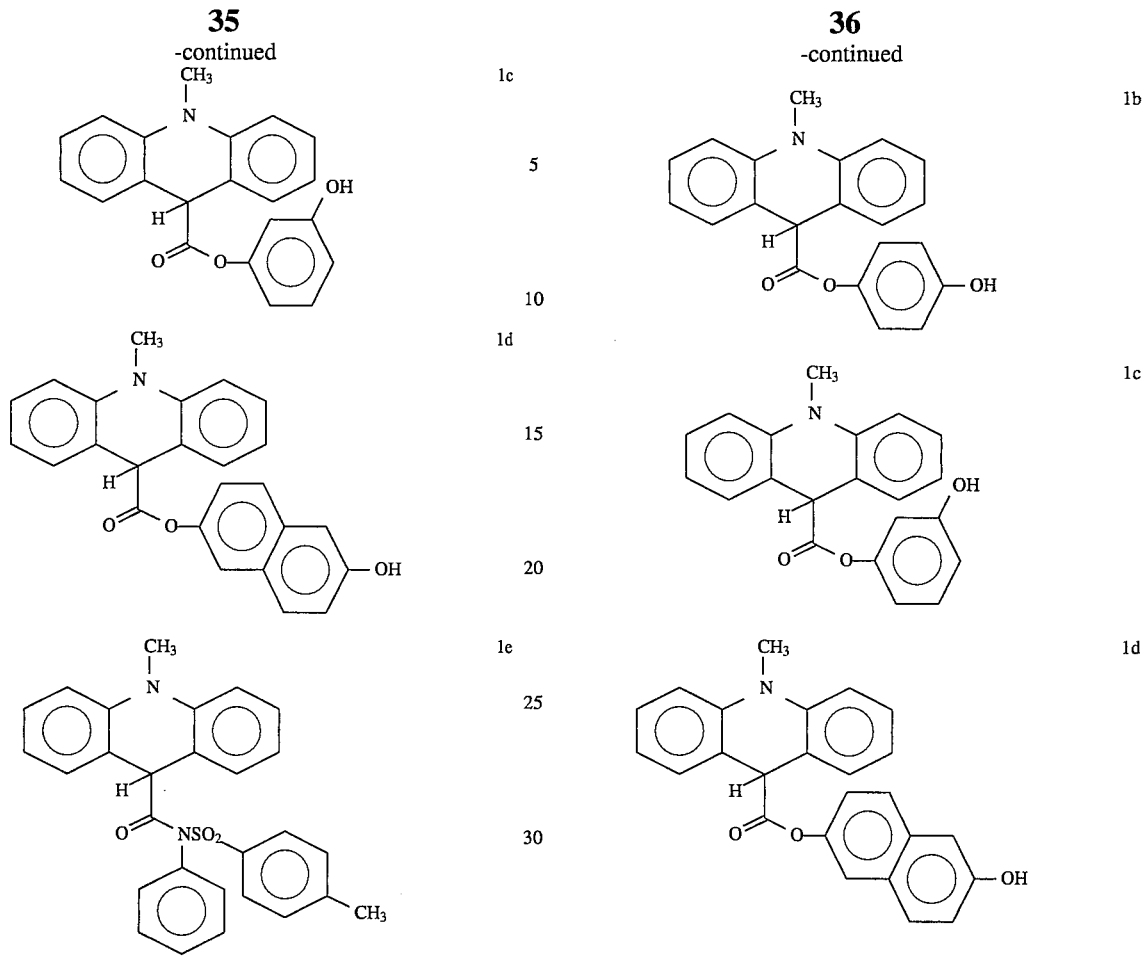

and the peroxidase is selected from the group consisting of horseradish peroxidase, microperoxidase and lactoperoxidase.

67. A method for detecting peroxidase selected from the group consisting of the peroxidase alone, organic molecules labeled with the peroxidase and biological molecules labeled with the peroxidase in an assay procedure by a chemiluminescent reaction comprising reacting in the presence of a peroxide an acridan selected from the group consisting of:

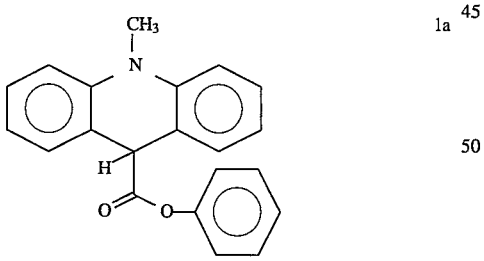

with the peroxidase to produce light.

68. The method of claim 67 wherein the peroxide is selected from the group consisting of hydrogen peroxide and perborate salts.

* * * * *